US009161969B2

(12) United States Patent
Shams

(10) Patent No.: US 9,161,969 B2
(45) Date of Patent: Oct. 20, 2015

(54) PROTECTION AGAINST INFLUENZA INFECTION BY GRANULOCYTE-MACROPHAGE COLONY STIMULATING FACTOR

(75) Inventor: Homayoun Shams, Tyler, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/006,854

(22) PCT Filed: Mar. 22, 2012

(86) PCT No.: PCT/US2012/030092
§ 371 (c)(1),
(2), (4) Date: Feb. 3, 2014

(87) PCT Pub. No.: WO2012/129385
PCT Pub. Date: Sep. 27, 2012

(65) Prior Publication Data
US 2014/0193506 A1 Jul. 10, 2014

Related U.S. Application Data

(60) Provisional application No. 61/466,354, filed on Mar. 22, 2011.

(51) Int. Cl.
*A61K 9/50* (2006.01)
*A61K 38/00* (2006.01)
*A61K 38/19* (2006.01)
*A61K 47/48* (2006.01)

(52) U.S. Cl.
CPC ......... *A61K 38/193* (2013.01); *A61K 47/48215* (2013.01); *A61K 47/48907* (2013.01)

(58) Field of Classification Search
None
See application file for complete search history.

(56) References Cited

U.S. PATENT DOCUMENTS

| | | | |
|---|---|---|---|
| 5,795,568 | A | 8/1998 | Wang |
| 6,019,965 | A | 2/2000 | Dunn et al. |
| 2004/0043446 | A1* | 3/2004 | DeFrees et al. ............. 435/68.1 |
| 2010/0015217 | A1 | 1/2010 | Fiala |

OTHER PUBLICATIONS

Kolchanov, 1988, Journal of Molecular Evolution, vol. 27, pp. 154-162.*
Pasquo, 2012, PLoS One, vol. 7, Issue 2, e32555.*
Bork, 2000, Genome Research 10:398-400.*
Bork et al., 1996, Trends in Genetics 12:425-427.*
Willenger et al. PNAS (2011), vol. 108, No. 6, pp. 2390-2395.*
Huang et al. Cytokine (2010), vol. 51, pp. 151-157.*
Extended European Search Report in Corresponding Case—Sep. 26, 2014.
Huang H et al., Protective effects of recombinant human granulocyte macrophage colony stimulating factor on H1N1 influenza virus-induced pneumonia in mice. Cytokine 51:151-157, 2010.
Lau YF et al. Activation of the innate immune system provides broad-spectrum protection against influenza A viruses with pandemic potential in mice. Virology 406:80-87, 2010.
Min L et al., Granulocyte-macrophage colony-stimulating factor is the major CD8+ T cell-derived licensing factor for dendritic cell activation. J Immunol 184:4625-4629, 2010.
Tuvim, MJ et al. Augmented Lung Inflammation Protects against Influenza A Pneumonia, PLoS One 4(1): 1-8, e4176 (Jan. 12, 2009).
Wang X et al., GM-CSF fused with GP3 and GP5 of porcine reproductive and respiratory syndrome virus increased the immune responses and protective efficacy against virulent PRRSV challenge. Virus Res 143:24-32, 2009.
Kim HM et al. Alveolar macrophages are indispensable for controlling influenza viruses in lungs of pigs. J Virol 82:4265-4274, 2008.
K. Sun and DW Metzger, Inhibition of pulmonary antibacterial defense by interferon-gamma during recovery from influenza infection. Nature Med. 14:556-564, 2003.
Orson FM et al. Protection against influenza infection by cytokine-enhanced aerosol genetic immunization. J. Gene Med 8:488-497, 2006.
Shi Y et al. Granulocyte-macrophage colony-stimulating factor (GM-CSF) and T cell responses: what we do and don't know. Cell Res 16:126-133, 2006.
Tazawa R et al. Granulocyte-macrophage colony-stimulating factor and lung immunity in pulmonary alveolar proteinosis. Am J Respir Crit Care Med 171:1142-1149, 2005.
Sasaki MD et al., Efficacy of granulocyte-macrophage colony-stimulating factor (GM-CSF) as a vaccine adjuvant for hepatitis B virus in patients with HIV infection. Vaccine 21:4545-9, 2003.

(Continued)

*Primary Examiner* — Christine J Saoud
*Assistant Examiner* — Jegatheesan Seharaseyon
(74) *Attorney, Agent, or Firm* — Browdy and Neimark, PLLC

(57) ABSTRACT

Alveolar macrophages contribute to host defenses against influenza. Enhancing their function contributed to protection against influenza and other acute lethal pulmonary infections. Wild-type mice and Tg mice expressing GM-CSF in the lung were infected with influenza virus, and lung pathology, weight loss and mortality were measured. GM-CSF was also administered to lungs of wild-type mice that were infected with influenza virus. All Tg mice expressing GM-CSF in the lungs survived with greatly reduced weight loss and lung injury and histologic evidence of a rapid host inflammatory response that controlled infection vs. wild-type mice not expressing GM-CSF in the lungs. This resistance to influenza was abrogated by elimination of alveolar phagocytes, but not by depletion of T cells, B cells or neutrophils. Tg mice had far more alveolar macrophages than wild-type mice and were more resistant to influenza-induced apoptosis. Delivery of intranasal GM-CSF to wild-type mice also conferred influenza resistance. Therefore, GM-CSF confers resistance to influenza by enhancing innate immune mechanisms that depend on alveolar macrophages. Pulmonary delivery of GM-CSF is therefore useful for reducing the significant morbidity and mortality due to influenza virus and is similarly useful in pulmonary infection caused by other infectious viral and bacterial agents.

14 Claims, 20 Drawing Sheets

(56) References Cited

OTHER PUBLICATIONS

Paine R, III, et al. Transgenic overexpression of granulocyte macrophage-colony stimulating factor in the lung prevents hyperoxic lung injury. Am J Pathol;163:2397-2406, 2003.

Paine R, III et al., Impaired functional activity of alveolar macrophages from GM-CSF-deficient mice. Am J. Physiol Lung Cell Mol Physiol 281:L1210-L1218, 2001.

Huber VC et al. Fc receptor-mediated phagocytosis makes a significant contribution to clearance of influenza virus infections. J Immunol 166:7381-7388, 2001.

Huffman Reed JA et al. GM-CSF enhances lung growth and causes aveolar type II epithelial cell hyperplasia in transgenic mice. Am J Physiol 273:L715-L725, 1997.

Huffman Reed JA et al., Pulmonary Epithelial Cell Expression of GM-CSF Corrects the Alveolar Proteinosis in GM-CSF-deficient Mice. J. Clin. Invest. 97:649-655, 1996.

Altamura M, et al., Successful treatment of herpes simplex virus (HSV) recurrent genital infection with recombinant human (rh) granulocyte-macrophage colony stimulating factor (GM-CSF): a case report. Immunopharmacol Immunotoxicol 19:425-36, 1997.

Martin J et al. Pilot study of recombinant human granulocyte-macrophage colony-stimulating factor in the treatment of chronic hepatitis B. Hepatology 18:775-80, 1993.

M.G. Manz, Human-Hemato-Lymphoid-System Mice: Opportunities and Challenges. Immunity 26;537-41, 2007.

A. Thomson (ed) The Cytokine Handbook, 3rd Ed. Acad Press, 1998 (single page, page number unknown).

F. Lee et al., Isolation of cDNA for a human granulocyte-macrophage colony-stimulating factor by functional expression in mammalian cells, Proc. Natl. Acad. Sci. USA 82:4360-64 (1985).

S. Miyatake et al., Structure of the chromosomal gene for granulocyte-macrophage colony stimulating factor: comparison of the mouse and human genes, EMBO J 4 2561-68 (1985).

K. Kaushansky et al. Hematopoietic activity of granulocyte/macrophage colony stimulating factor is dependent upon two distinct regions of the molecule: Functional analysis based upon the activities of interspecies hybrid growth factors Proc. Natl. Acad. Sci. U.S.A. 86:1213-17 (1989).

A.B. Shanafelt et al. Identification of Critical Amino Acid Residuesin Human and Mouse Granulocyte-Macrophage Colony-stimulating Factor and Their Involvement in Species Specificity. J. Biol. Chem. 266:13804-10 (1991).

K. Diederichs et al., Novel Fold and Putative Receptor Binding Site of Granulocyte-Macrophage Colony-Stimulating Factor, Science 254:1779-82 (1991).

T.R. Hercus et al. Identification of Residues in the First and Fourth Helices of Human Granulocyte-Macrophage Colony-Stimulating Factor Involved in Biologic Activity and in Binding to the a- and •-Chainsof Its Receptor. Blood, 83:3500-3508 (1994).

A. Miyajama et al., Receptors for Granulocyte-Macrophage Colony-Stimulating Factor, Interleukin-3, and Interleukin-5, Blood, 82:1960-74 (1993).

I. Nishijima et al., A Human GM-CSF Receptor Expressed in Transgenic Mice Stimulates Proliferation and Differentiation of Hemopoietic Progenitors to All Lineages in Response to Human GM-CSF, Mol Biol. Cell. 6;497-508 (1995).

Renuka Subramaniam, Zachary Hillberry, Han Chen, Pierre Neuenschwander and Homayoun Shams, Pathology and protection in influenza pneumonia, (manuscript submitted to PLoS One, Feb. 2015).

* cited by examiner

PROTECTION AGAINST INFLUENZA INFECTION BY GRANULOCYTE-MACROPHAGE COLONY STIMULATING FACTOR

BACKGROUND OF THE INVENTION

1. Field of the Invention

The invention in the field of medicine and immunology, particularly innate immunity, relates to prevention and treatment of influenza infections with granulocyte-macrophage colony stimulating factor (GM-CSF) and to the prevention and treatment of acute pneumonia caused by other organisms.

2. Description of the Background Art

Seasonal influenza causes an estimated three to five million cases and 250,000 to 500,000 deaths worldwide annually. (See, for example, URL: who.int/mediacentre/factsheets/fs211/en/.) Pandemic disease can result in substantial additional morbidity, mortality and economic cost, as evidenced by the recent H1N1 swine influenza pandemic. The tremendous human burden of influenza mandates improved methods to prevent and treat this infection.

Control and clearance of influenza infection are believed to hinge on adaptive immunity, mediated by B and T lymphocytes. B cells produce antibodies to influenza hemagglutinin and neuraminidase, which protect against homologous virus (1). CD8+ cytolytic (or cytotoxic) T lymphocytes (CTL) cells clear influenza virus, limit viral replication and protect against lethal virus challenge (2-6). Recent studies also suggest a protective role for CD4+ T cells (7-10), which can lyse infected target cells (8), provide help to B cells, and promote expansion of CD8+ CTL (9). Based on the strength of the understanding that adaptive immunity is central to protection against influenza, preventive strategies have focused primarily on development of vaccines. Unfortunately, vaccines have been variably effective, in part because of antigenic shift and drift in the influenza viruses circulating in the population.

Recent studies have shown that innate immunity is also critical for resistance to influenza (11). Alveolar macrophages (AM) are the first line of host defense against respiratory microbes in general, and they contribute to clearance of influenza virus by Fc receptor-mediated phagocytosis (12). Depletion of AM markedly enhances disease severity caused by influenza in murine and porcine experimental models (13, 14). However, the mechanisms by which AM mediate protection are not well understood.

Granulocyte macrophage colony stimulating factor (GM-CSF) activity of was initially discovered in lung cell-conditioned medium where it stimulated growth of granulocytes and macrophages from cultured hematopoietic progenitors (Metcalf D. *Blood* 111:485-91, 2008). The nucleotide and amino acid sequences of murine and human GM-CSF (hGM-CSF) have been known for many years (Wong G G et al., *Science* 228:810-15 (1985); Lee, F, et al. *Proc. Natl. Acad. Sci. USA* 82:4360-4364, 1985; Miyatake, S et al., *EMBO J* 4:2561-68, 1985). hGM-CSF has been produced recombinantly in bacterial, yeast, mammalian, plant, and insect expression systems (see, fore example, Babu K S et al., *Biotechnol Lett* 31:659-64, 2009; Sardana R et al., *Transgenic Res* 16:713-21, 2008; Kim N S et al., *Plant Mol Biol* 68:263-75, 2008).

Recombinant hGM-CSF (rhGM-CSF) is most commonly used to promote hematopoietic recovery after cancer chemotherapy and bone marrow transplantation. This protein has additional biologic effects in activating immune responses to infection and inflammation, and in hematopoiesis (Sasaki M G et al., *Vaccine* 21:4545-9, 2003). rhGM-CSF has therefore been was used in clinical treatment of infectious disease, malignancies, wound healing and other conditions (Wang X L et al., *Virus Res* 143:24-32, 2009; Coon C et al., *Scand J Immunol* 70:106-15, 2009; Jin S et al., *Cancer Biother Radiopharm* 24:237-41, 2009; Lutzky J et al., *J Immunother* 32:79-85, 2009; Sato T et al., *J Clin Oncol* 26:5436-42, 2008; Dai S et al., *Mol Ther* 16:782-90, 2008; Mann A et al., *J Investig Dermatol, Symp Proc* 11:87-92, 2006)

Therapeutic antiviral activity has been observed with rhGM-CSF used as an immunological adjuvant or in combination with antivirals (Sasaki et al., supra; Elias E G et al., *Cancer Biother Radiopharm* 23:285-91, 2008; Qiu J T et al., *Vaccine* 25:253-63, 2007; Zhai Y Z et al., *Intervirology* 52:152-63, 2009). Antiviral effects of rhGM-CSF alone against hepatitis B virus (Martin J et al. *Hepatology* 1993; 18:775-80, 1993), HIV (Matsuda S et al., *AIDS Res Hum Retrovir* 11:1031-8, 1995) and Herpes simplex virus (Altamura M, et al., *Immunopharmacol Immunotoxicol* 19:425-36, 1997) have been reported.

GM-CSF contributes to maturation of mononuclear phagocytes and AM (15, 16). In patients with pulmonary alveolar proteinosis, circulating neutralizing antibodies against GM-CSF cause AM dysfunction (17), and AM from GM-CSF-deficient (GM-/-) mice have impaired capacity for phagocytosis and cytokine production, which functions were restored by GM-CSF treatment (18). Studies in GM-/- mice showed that GM-CSF contributed to immune responses during pneumonia that was caused by *Pseudomonas aeruginosa* and *Pneumocystis carinii*; administration of GM-CSF to septic patients reversed monocyte immunosuppression and improved the clinical course (19-21). DNA vaccination with a plasmid encoding influenza hemagglutinin, GM-CSF and IL-12 resulted in reduced viral titers and increased neutralizing antibody titers (22), suggesting that GM-CSF may enhance adaptive immune responses.

Huang H et al., showed protective effects of recombinant human GM-CSF on H1N1 influenza virus-induced pneumonia in mice (23).

Secondary bacterial infection occurs commonly after pulmonary virus infection and can cause severe disease in humans. Mechanisms responsible for this "synergy" in the lung are poorly understood. K. Sun and D W Metzger reported (*Nature Med.* 14:558-564 (2008)) that in mice, pulmonary interferon-γ (IFNγ) produced during the T cell response to influenza infection inhibited initial bacterial clearance from the lung by AM. This suppression of phagocytosis which correlated with lung IFNγ levels but not with viral burden, resulted in enhanced susceptibility to secondary pneumococcal infection. This effect could be prevented by neutralizing IFNγ after influenza infection. Thus, while promoting induction of anti-influenza adaptive immunity, this T cell product of the immune response, IFNγ, suppressed innate protection against extracellular bacterial pathogens in the lung.

In response to the need in the art for improved approaches to prevent and treat influenza infections, the present inventor conceived of the present invention.

(Certain references above and below appear as parenthetical numbers and appear in a reference list. Others are provided directly in the body of the text.) Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors conceived that enhancing the functional capacities alveolar macrophages (AM) would increase resistance to influenza infection. Using as a model mice that transgenically express GM-CSF only in the lung, they determined that GM-CSF upregulates innate and adaptive immunity to influenza infection.

Most studies of the immune response to influenza have focused on the importance of antibody production by B cells and cytolytic activity of CD8+ T cells in mediating protection against infection. The present invention provides a novel means of conferring marked resistance to influenza (and other viruses) by enhancing innate immune mechanisms that depend on AM.

The present invention provides a method of stimulating the influenza-resisting activity of AM comprising providing to the AM a source of human GM-CSF (hGM-CSF) that stimulates the activity.

Also provided is a method of stimulating innate immunity in the lungs of a subject, preferably a human, which innate immunity is capable of increasing homeostasis of lung and suppressing development of influenza infection in the lungs, comprising, administering to the lungs of the subject an effective amount of a source of hGM-CSF, thereby stimulating the innate immunity. This may also be used to suppress development of hantavirus infections.

The invention includes a method of suppressing lung injury and influenza infection, comprising administering to a subject infected with influenza virus an effective amount of a source of hGM-CSF, thereby suppressing lung damages due to and the infection.

Also provided is a method of preventing the development of an influenza infection in a subject susceptible thereto, comprising administering to the lungs of the subject prior to infection with influenza virus an effective preventative amount of a source of hGM-CSF, thereby preventing the development of the infection.

The present invention is further used to treat established pneumonia in lungs of subjects who have been infected, for example, with influenza or other viruses, or various bacterial species as is disclosed below.

In the above methods, the source of hGM-CSF is preferably administered to the lungs, most preferably by intranasal administration. The hGM-CSF (or functional variant or derivative) maybe administered as an aerosol.

In the above methods the source of the hGM-CSF is preferably a recombinant hGM-CSF ("rhGM-CSF") polypeptide or a functional variant thereof that includes hGM-CSF that is conjugated or covalently bonded to other molecules. Most preferably, the hGM-CSF has the sequence SEQ ID NO:4. The hGM-CSF is preferably encoded by a DNA molecule the nucleotide sequence of which is SEQ ID NO:3. In the above method, the functional variant is preferably a conservative amino acid substitution variant of SEQ ID NO:4.

The rhGM-CSF, or a functional variant or derivative, may be conjugated to a delivery agent, preferably a nanoparticle or to polyethylene glycol (PEG) and in this form is (i) retained better in the lung to promote the biological effects on AM and (ii) prevented from entering the circulation to avoid potential systemic toxic effects from high doses of the GM-CSF. This use is particularly well suited for treating acute pulmonary infections/pneumonia that has been established as a result of infection by, e.g., influenza virus, hantavirus, or other infectious agents.

In the foregoing methods the source of the hGM-CSF may be a recombinant DNA molecule that encodes a hGM-CSF polypeptide or encodes a functional variant thereof, which DNA molecule is expressed in human lung cells. Preferably, the DNA molecule comprises the nucleotide sequence SEQ ID NO:3. In one embodiment, the DNA molecule encodes a functional variant of hGM-CSF, more preferably, an amino acid sequence variant, most preferably, a conservative amino acid sequence variant.

BRIEF DESCRIPTION OF THE DRAWINGS

(FIG. 10A) Representative dot plots show the percentages of F4/80+Annexin V+ cells. (FIG. 10B) show results with gating on F4/80+ cells and measurement of mean fluorescence intensity (MFI) of Fas. Representative histograms show Fas expression on F4/80+ cells. Values in each histogram show the net MFI of Fas expression: MFI of the isotype control (filled histograms) subtracted from MFI of Fas (open histograms). Representative result of two SPC-GM and two WT mice are shown.

DESCRIPTION OF THE PREFERRED EMBODIMENTS

Figure 1A:
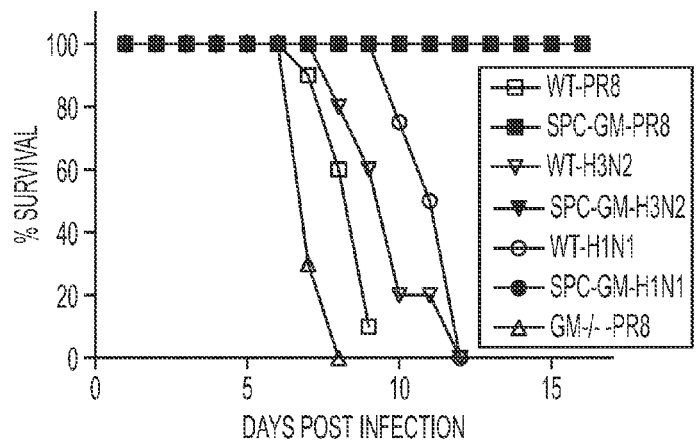
FIG. 1. Pulmonary GM-CSF Expression Protects Against Influenza. (A) WT, GM−/− and SPC-GM mice (n=10/group, result representative of 3 experiments) were infected with 5 $LD_{50}$ of influenza A virus PR8. WT and SPC-GM mice were infected with lethal doses of H3N2 HK68 (n=5/group) or mouse-adapted H1N1 swine influenza (n=4/group). All mice were followed until death or recovery. (B) WT, GM−/− and SPC-GM mice (n=8/group) were infected with 5 $LD_{50}$ of PR8, and weighed daily until death or recovery. Means±SE are shown. (C) WT mice were given a polyethyleneimine-coated GM-CSF expression vector or a control empty vector (n=7-8/group) by retro-orbital injection. 4-6 weeks later, mice were infected with 2 $LD_{50}$ of PR8, and followed until death or recovery (p=0.0008, comparing treatment with GM-CSF-expressing vector and empty vector). In an independent experiment, mice were treated with PBS (n=5/group) or rGM-CSF intranasally for 7 days (n=6/group), then infected 1 day later with 2 $LD_{50}$ of PR8 (p=0.008, comparing rGM-CSF-treated and PBS-treated mice). Results are representative of 2-5 experiments.

Strategies to protect against influenza have focused on development of antiviral drugs and enhancing the adaptive immune response through vaccination. Little information is available on harnessing innate immunity to protect against influenza.

The present invention is based on the discovery that enhancing the functional capacities of alveolar macrophages (AM) using GM-CSF increases resistance to influenza infection and GM-CSF upregulates innate and adaptive immunity to influenza infection and thereby is useful for limiting, attenuate, and decreasing the infection and thereby providing protection against what would be lethal influenza in subjects. The present approach is similarly applicable to other virus infections, particularly hantavirus infection in humans. The invention is not limited to human subjects, but may similarly be used in other mammals in the practice of veterinary medicine.

Exemplification was primarily in a murine transgenic ("Tg") disease model in which murine GM-CSF (mGM-CSF) was expressed in the lungs. Protection depended on alveolar macrophages, but not on T cells or B cells.

The nucleotide and amino acid sequences of murine GM-CSF (mGM-CSF) can be found in GenBank, NCBI Reference Sequence: NM_009969.4

DNA encoding murine GM-CSF has the following nucleotide sequence SEQ ID NO:1 (not showing the stop codon):

```
atg tgg ctg cag aat tta ctt ttc ctg ggc att gtg gtc tac agc ctc tca gca ccc acc cgc tca ccc atc act gtc acc cgg cct tgg aag cat gta gag gcc atc aaa gaa gcc ctg aac ctc ctg gat gac atg cct gtc acg ttg aat gaa gag gta gaa gtc gtc tct aac gag ttc tcc ttc aag aag cta aca tgt gtg cag acc cgc ctg aag ata ttc gag cag ggt cta cgg ggc aat ttc acc aaa ctc aag ggc gcc ttg aac atg aca gcc agc tac tac cag aca tac tgc ccc cca act ccg gaa acg gac tgt gaa aca caa gtt acc acc tat gcg gat ttc ata gac agc ctt aaa acc ttt ctg act gat atc ccc ttt gaa tgc aaa aaa cca ggc caa aaa
```

The murine GM-CSF protein (141 amino acids) has the following sequence SEQ ID NO: 2

| | | | | | | | | | | | | | | | | |
|---|---|---|---|---|---|---|---|---|---|---|---|---|---|---|---|---|
| *Met* | *Trp* | *Leu* | *Gln* | *Asn* | *Leu* | *Leu* | *Phe* | *Leu* | *Gly* | *Ile* | *Val* | *Val* | *Tyr* | *Ser* | *Leu* | 16 |
| *Ser* | Ala | Pro | Thr | Arg | Ser | Pro | Ile | Thr | Val | Thr | Arg | Pro | Trp | Lys | His | 32 |
| Val | Glu | Ala | Ile | Lys | Glu | Ala | Leu | Asn | Leu | Leu | Asp | Asp | Met | Pro | Val | 48 |
| Thr | Leu | Asn | Glu | Glu | Val | Glu | Val | Val | Ser | Asn | Glu | Phe | Ser | Phe | Lys | 64 |
| Lys | Leu | Thr | Cys | Val | Gln | Thr | Arg | Leu | Lys | Ile | Phe | Glu | Gln | Gly | Leu | 80 |
| Arg | Gly | Asn | Phe | Thr | Lys | Leu | Lys | Gly | Ala | Leu | Asn | Met | Thr | Ala | Ser | 96 |
| Tyr | Tyr | Gln | Thr | Tyr | Cys | Pro | Pro | Thr | Pro | Glu | Thr | Asp | Cys | Glu | Thr | 112 |
| Gln | Val | Thr | Thr | Tyr | Ala | Asp | Phe | Ile | Asp | Ser | Leu | Lys | Thr | Phe | Leu | 128 |
| Thr | Asp | Ile | Pro | Phe | Glu | Cys | Lys | Lys | Pro | Gly | Gln | Lys | | | | 141 |

Residues 1-17 are the signal peptide; the mature peptide begins at position 18 (Ala).

The nucleotide and amino acid sequences of human GM-CSF (hGM-CSF) can be found in GenBank, NCBI Reference Sequence: NM_000758.2. See also Wong G G et al., supra; Lee, F, et al., supra Miyatake et al., supra)

DNA encoding human GM-CSF has the following nucleotide sequence, SEQ ID NO:3 (not showing the stop codon):

```
atg tgg ctg cag agc ctg ctg ctc ttg ggc act gtg gcc tgc agc atc tct gca ccc gcc cgc tcg ccc agc ccc agc acg cag ccc tgg gag cat gtg aat gcc atc cag gag gcc cgg cgt ctc ctg aac ctg agt aga gac act gct gct gag atg aat gaa aca gta gaa gtc atc tca gaa atg ttt gac ctc cag gag ccg acc tgc cta cag acc cgc ctg gag ctg tac aag cag ggc ctg cgg ggc agc ctc acc aag ctc aag ggc ccc ttg acc atg atg gcc agc cac tac aag cag cac tgc cct cca acc ccg gaa act tcc tgt gca acc cag att atc acc ttt gaa agt ttc aaa gag aac ctg aag gac ttt ctg ctt gtc atc ccc ttt gac tgc tgg gag cca gtc cag gag
```

The human GM-CSF protein (144 amino acids) has the following amino acid sequence SEQ ID NO: 4:

| | | | | | | | | | | | | | | | | |
|---|---|---|---|---|---|---|---|---|---|---|---|---|---|---|---|---|
| *Met* | *Trp* | *Leu* | *Gln* | *Ser* | *Leu* | *Leu* | *Leu* | *Leu* | *Gly* | *Thr* | *Val* | *Ala* | *Cys* | *Ser* | *Ile* | 16 |
| *Ser* | Ala | Pro | Ala | Arg | Ser | Pro | Ser | Pro | Ser | Thr | Gln | Pro | Trp | Glu | His | 32 |
| Val | Asn | Ala | Ile | Gln | <u>Glu</u> | Ala | Arg | Arg | Leu | Leu | Asn | Leu | Ser | Arg | Asp | 48 |

-continued

| | | | | | | | | | | | | | | | |
|---|---|---|---|---|---|---|---|---|---|---|---|---|---|---|---|
| Thr | Ala | Ala | Glu | Met | Asn | Glu | Thr | Val | Glu | Val | Ile | Ser | Glu | Met | Phe | 64 |
| Asp | Leu | Gln | Glu | Pro | Thr | Cys | Leu | Gln | Thr | Arg | Leu | Glu | Leu | Tyr | Lys | 80 |
| Gln | Gly | Leu | Arg | Gly | Ser | Leu | Thr | Lys | Leu | Lys | <u>Gly</u> | Pro | Leu | Thr | Met | 96 |
| Met | Ala | Ser | His | Tyr | Lys | <u>Gln</u> | His | Cys | Pro | Pro | Thr | Pro | Glu | Thr | Ser | 112 |
| Cys | Ala | Thr | Gln | Ile | Ile | Thr | Phe | Glu | Ser | Phe | Lys | Glu | Asn | Leu | Lys | 128 |
| Asp | Phe | Leu | Leu | Val | Ile | Pro | Phe | Asp | Cys | Trp | Glu | Pro | Val | Gln | Glu | 144 |

Residues 1-17 (in italic) are the signal peptide; the mature peptide begins at position 18 (Ala). The three underscored residues are discussed below.

The core of hGM-CSF consists of four helices that pack at angles that distinguishes this structure from known antiparallel four-helix bundle proteins. The amino acid sequence properties and previous structural characterizations of GM-CSF led to an assignment of the probable protein segments that form the helices (from low-resolution X ray structure (6 Å) (Diederichs, K et al., *J Mol Biol.* 221:55-60, 1991). Refined crystal structure (~2.4 Å along a* and approximately 1.9 Å along b* and c*) and mutagenic analysis of rhGM-CSF (Rozwarski D A et al., *Proteins* 26:304-13, 1996) showed that, in addition to apolar side chains in the protein core, 10 buried hydrogen bonding residues involve intramolecular hydrogen bonding to main chain atoms that were better conserved than residues hydrogen bonding to other side chain atoms; 24 solvation sites were observed at equivalent positions in the two molecules in the asymmetric unit, and the strongest among these was located in clefts between secondary structural elements. No buried water sites were seen. Two surface clusters of hydrophobic side chains are located near the expected receptor binding regions. Mutagenesis of 11 residues on the helix A/helix C face confirmed the importance of Glu-21 (position 38 in SEQ ID NO:4 because the signal peptide is included) and showed that Gly-92 (of SEQ ID NO:4) and Gln-103 (of SEQ ID NO:4), located on helix C, each cause a greater than fourfold drop in activity. The Glu-38, and the Gly-92, but not the Glu-103 are structurally equivalent to residues involved in the growth hormone binding to its receptor.). These residues are therefore not to be substituted in the functional substitution variants of hGM-CSF for use in the present invention and these helices are to be retained in a functional fragments or deletion variants of hGM-CSF for use in this invention.

N-terminal helix of hGM-CSF governs high affinity binding to its receptor (Shanafelt A B et al., *EMBO J* 10:4105-12, 1991) Transduction of the biological effects of GM-CSF requires interaction with at least two cell surface receptor components, (one of which is shared with the cytokine IL-5). The above study identified receptor binding determinants in GM-CSF by locating unique receptor binding domains on a series of human-mouse hybrid GM-CSF cytokines. The interaction of GM-CSF with the shared subunit of their high affinity receptor complexes was governed by a very small part of the peptide chains. The presence of a few key residues in the N-terminal α-helix of was sufficient to confer specificity to the interaction. Comparison with other cytokines suggested that the N-terminal helix of many of these proteins may contain the recognition element for the formation of high affinity binding sites with the α subunit of the multi-component receptor. GM-CSF low and high affinity receptors are described (briefly) below.

Human GM-CSF Receptors (hGM-CSF-R)

The hGM-CSF-R, cloned and sequenced in 1989 (Gearing, D P et al., *EMBO J.* 8:3667-3676, 19890 exhibits low-affinity binding for hGM-CSF (when that latter was expressed on COST cells). Although GM-CSF induces tyrosine phosphorylation, no tyrosine kinase consensus sequence was found The functional high-affinity GM-CSF receptor is composed of multiple subunits, one of which is shared with the human IL-3 receptor. Hayashida, K et al. (*Proc Natl Acad Sci USA* 87:9655-9, 1990) cloned a human cDNA homologous with the murine IL-3 receptor cDNA. The encoded protein alone did not bind GM-CSF, IL-3 or other cytokines but rather conferred high-affinity binding for hGM-CSF when cotransfected with the low-affinity hGM-CSF receptor cDNA. This cDNA (KH97) therefore encoded a second subunit of the high-affinity hGM-CSF receptor. The low-affinity GM-CSF receptor as designated as the α subunit and the "KH97 protein" as the β subunit of the GM-CSF-R Several transcription variants of the hGM-CSF-R gene are known, and their sequences are found in Genbank, e.g., NCBI Reference Sequences: NM_006140.4 (Variant 1), 172245.2 (Variant 2) and NM_172246.2 (Variant 3). Four additional variants numbered 4-7 are also in the database. Transcript Variants 1, 2 and 7 encode the same protein isoform (a), which is membrane-bound. Transcript Variant 2: differs in the 5' UTR compared to variant 1. The protein of variants 1 and 2 is shown below as SEQ ID NO:5, Transcript Variant 3 lacks two coding exons in the 3' region, which causes a frameshift, compared to Variant 1. The resulting isoform (b), which is likely soluble, is shorter and has a distinct C-terminus (SEQ ID NO:6 below). In both SEQ ID NO:5 and 6, the first 57 residues are the signal peptide and the remaining residues constitute the mature protein.

```
SEQ ID NO: 5:
MLLLVTSLLLCELPHPAFLLIPEKSDLRTVAPASSLNVRFDSRTMNLSWD      50

CQENTTFSKCFLTDKKNRVVEPRLSNNECSCTFREICLHEGVTFEVHVNT     100

SQRGFQQKLLYPNSGREGTAAQNFSCFIYNADLMNCTWARGPTAPRDVQY     150

FLYIRNSKRRREIRCPYYIQDSGTHVGCHLDNLSGLTSRNYFLVNGTSRE     200

IGIQFFDSLLDTKKIERFNPPSNVTVRCNTTHCLVRWKQPRTYQKLSYLD     250
```

```
                              -continued
FQYQLDVHRKNTQPGTENLLINVSGDLENRYNFPSSEPRAKHSVKIRAAD             300

VRILNWSSWSEAIEFGSDDGNLGSVYIYVLLIVGTLVCGIVLGFLFKRFL             350

RIQRLFPPVPQIKDKLNDNHEVEDEIIWEEFTPEEGKGYREEVLTVKEIT             400

SEQ ID NO: 6
MLLLVTSLLLCELPHPAFLLIPEKSDLRTVAPASSLNVRFDSRTMNLSWD              50

CQENTTFSKCFLTDKKNRVVEPRLSNNECSCTFREICLHEGVTFEVHVNT             100

SQRGFQQKLLYPNSGREGTAAQNFSCFIYNADLMNCTWARGPTAPRDVQY             150

FLYIRNSKRRREIRCPYYIQDSGTHVGCHLDNLSGLTSRNYFLVNGTSRE             200

IGIQFFDSLLDTKKIERFNPPSNVTVRCNTTHCLVRWKQPRTYQKLSYLD             250

FQYQLDVHRKNTQPGTENLLINVSGDLENRYNFPSSEPRAKHSVKIRAAD             300

VRILNWSSWSEAIEFDHLGGIHPRGRERLPRRGLDREGNYLRPRGCRNGM             350

DISASATRGNFLDDAVNLYIFYVFI                                      375
```

Functional Variants of GM-CSF

Modifications and changes may be made in the sequence of hGM-CSF according to the present invention, to create molecules with similar or improved anti-influenza characteristics. Such functional variants or biologically active variants (which terms are used interchangeably) are encompassed within the present invention.

A preferred functional variant of hGM-CSF is an amino acid substitution variant that retains the biological and biochemical activity of the parent GM-CSF, such as the binding to high affinity GM-CSF-R and, the cellular (e.g., colony stimulating) and anti-influenza activity of GM-CSF.

Also included in the invention are deletion variants, addition variants, as well as fusion constructs, etc Important residues and regions to be preserved in such variants were noted above.

It is well-known that certain amino acids may be substituted for others in a peptide or polypeptide without appreciable loss of biochemical activity such as binding to ligands and post-binding biological activity. Examples are antigen-binding regions of antibodies, ligand binding sites on substrate molecules or receptors, etc. When a peptide or polypeptide functions by in interacting with another molecule, such as another protein, polypeptide or peptide, such an interaction defines the molecule's biological functional activity. It is well known that certain amino acid substitutions can be made in proteinaceous molecules while retaining the relevant interactive, e.g., binding properties.

It is thus contemplated that various changes may be made in the sequence of GM-CSF without appreciable loss of their biological activity or their utility in accordance with this invention.

Any variant or fragment of hGM-CSF can be test for suitability with the present invention by testing its binding to a GM-CSF-R (cell bound or soluble) or by its biological activity in an in vitro or in vivo assay.

Binding to a soluble receptor (e.g., a protein with the sequence SEQ ID NO:6) can be performed in any conventional binding assay utilizing appropriate colored, enzymatic or radiolabel. Binding to a cellular receptor, e.g., a protein with the sequence SEQ ID NO:5 expressed natively or recombinantly on a cell surface, can be measured by conventional means. A competitive assay can also be used in which the test substance is unlabeled and its ability to inhibit or prevent binding of hGM-CSF to its receptor is measured.

A preferred way to measure the biological activity of the variant is in any of a number of bioassays for GM-CSF activity that are well known in the art.

Amino Acid Substitution (and Addition) Variants

GM-CSF substitution variants of the present invention preferably have no more than five conservative substitutions, preferably no more than four, preferably no more than three, preferably nor more than two and more preferably no more than one substituted amino acid residue, In terms of functional equivalents, it is well understood by those skilled in the art that inherent in the definition of a "biologically functional equivalent" protein, polypeptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those polypeptides/peptides in which certain, not most or all, of the amino acids may be substituted.

In particular, the shorter the length of the polypeptide, the fewer amino acids changes should be made. Longer polypeptides than SEQ ID NO:4 fragments may have an intermediate number of changes. The full length polypeptide protein will have the most tolerance for a larger number of changes. It is also well understood that where certain residues are shown to be particularly important to the biological or structural properties of a polypeptide residues in a binding regions or an active site, such residues may not generally be exchanged. In this manner, functional equivalents are defined herein as those poly peptides which maintain a substantial amount of their native biological activity.

For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups shown in the table below.

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

| 1 | Small aliphatic, nonpolar or slightly polar residues | Ala, Ser, Thr (Pro, Gly); |
|---|---|---|
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The hydropathy index of amino acids may also be considered in selecting variants. Each amino acid has been assigned a hydropathy index on the basis of their hydrophobicity and charge characteristics, these are: Ile (+4.5); Val (+4.2); Leu (+3.8); Phe (+2.8); Cys (+2.5); Met (+1.9); Ala (+1.8); Glycine (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). The importance of the hydropathy index in conferring interactive biological function on a proteinaceous molecule is generally understood in the art (Kyte and Doolittle, 1982, *J. Mol. Biol.* 157:105-32). It is known that certain amino acids may be substituted for other amino acids having a similar hydropathy index or score and still retain a similar biological activity. In making changes based upon the hydropathy index, the substitution of amino acids whose hydropathy indices are within ±2 is preferred, those which are within ±1 are particularly preferred, and those within ±0.5 are even more particularly preferred. It is also understood in the art that the substitution of like amino acids can be made effectively on the basis of hydrophilicity, particularly where the biological functional equivalent polypeptide thereby created is intended for use in certain of the present embodiments. U.S. Pat. No. 4,554,101, discloses that the greatest local average hydrophilicity of a proteinaceous molecule, as governed by the hydrophilicity of its adjacent amino acids, correlates with a biological property of the molecule. See U.S. Pat. No. 4,554,101 for a hydrophilicity values. In making changes based upon similar hydrophilicity values, the substitution of amino acids whose hydrophilicity values are within ±2 is preferred, those which are within ±1 are particularly preferred, and those within ±0.5 are even more particularly preferred.

Most substitutions according to the present invention are those that do not produce marked diminution in the functional characteristics of the peptide molecule. Even when it is difficult to predict the exact effect of a substitution in advance, one skilled in the art will appreciate that the effect can be evaluated by routine screening assays, preferably the binding assay or biological assays (described and/or exemplified herein). Modifications of peptide properties including redox or thermal stability, hydrophobicity, susceptibility to proteolytic degradation are tested by methods well known to those of skill in the art. It will be appreciated that that loss of stability, increase in tendency to aggregate, increased susceptibility to proteolysis, etc., are to be avoided.

Included in within the definition of functional variants of GM-CSF are addition variants which preferably comprise additional amino acids at either terminus or at both termini. In other embodiments, further additional residues may be added, as long as the polypeptide does not exceed a total length of about 200 residues. The additional residues may be added not only to SEQ ID NO:4 but also to the functional variants thereof, such as to conservative substitution variants.

It is understood that in a case in which one or more residues are shown to be particularly important to the biological function or structural integrity of a polypeptide herein, such as residues in a binding region, such residues generally are not to be varied. In this manner, functional variants defined herein as those polypeptides which maintain a substantial amount of the biochemical or biological activity of the native or reference polypeptide can be identified.

A preferred composition is, or comprises, a biologically active variant or derivative of human GM-CSF characterized in that it possesses the binding activity and/or biological activity of hGM-CSF as described herein. A biologically active variant has the activity of hGM-CSF in an in vitro or in vivo assay. Preferably the functional variant has at least about 20% of the activity of hGM-CSF, preferably at least 30%, more preferably at least 40%, more preferably at least 50%, more preferably at least 60%, more preferably at least 70%, more preferably at least 80%, more preferably at least 90%, more preferably at least 95%. The variant may have 100% or even greater activity than hGM-CSF.

Chemical Derivatives of hGM-CSF

"Chemical derivatives" of hGM-CSF contain additional chemical moieties not normally a part of a protein. Covalent modifications of the polypeptide are included within the scope of this invention. Such derivatized moieties may improve the solubility, absorption, biological half life, and the like. Moieties capable of mediating such effects are disclosed, for example, Gennaro, A R, *Remington: The Science and Practice of Pharmacy*, Lippincott Williams & Wilkins Publishers; 21$^{st}$ Ed, 2005 (or latest edition)

Such modifications may be introduced into the molecule by reacting targeted amino acid residues of the polypeptide with an organic derivatizing agent that is capable of reacting with selected side chains or terminal residues. Another modification is cyclization of the protein or a portion thereof.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5-7.0) which agent is relatively specific for the histidyl side chain. p-bromophenacyl bromide also is useful; the reaction is preferably performed in 0.1 M sodium cacodylate at pH 6.0.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high $pK_a$ of the guanidine functional group. Furthermore, these reagents may react with the groups of lysine as well as the arginine ε-amino group.

Modification of tyrosyl residues has permits introduction of spectral labels into a polypeptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions.

Derivatization with bifunctional agents is useful for cross-linking the polypeptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl groups. Also included are polypeptides wherein one or more D-amino acids are substituted for one or more L-amino acids.

Production of Peptides, Polypeptides and Derivatives

General Chemical Synthetic Procedures

Shorter polypeptide fragments, e.g., between about 15 and about 40 amino acids in length are preferably prepared using solid-phase synthesis such as that generally described by Merrifield, *J. Amer. Chem. Soc.*, 85:2149-54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin. Such methods, well-known in the art, are disclosed, for example, in U.S. Pat. No. 5,994,309 which is incorporated by reference in its entirety.

hGM-CSF or a functional variant sequence thereof, may be prepared using recombinant DNA technology or by fusion or chemical conjugation to other molecules. Preferred vectors used in the present examples are described herein.

Basic texts disclosing general methods of molecular biology, all of which are incorporated by reference, include: Sambrook, J. et al., *Molecular Cloning: A Laboratory Manual*, $2^{nd}$ Edition, Cold Spring Harbor Press, Cold Spring Harbor, N.Y., 1989; Ausubel, F M et al. *Current Protocols in Molecular Biology, Vol. 2*, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, $2^{nd}$ Ed., Garland Publishing, Inc., New York, N.Y. (1989); Watson, J D et al., *Recombinant DNA*, $2^{nd}$ Ed., Scientific American Books, New York, 1992; and Old, R W et al., *Principles of Gene Manipulation: An Introduction to Genetic Engineering*, $2^{nd}$ Ed., University of California Press, Berkeley, Calif. (1981).

Vectors

According to the various embodiments of the present invention, a variety of known nucleic acid vectors may be used in these methods, e.g., recombinant viruses, such as recombinant adeno-associated virus (rAAV), recombinant adenoviruses, recombinant retroviruses, recombinant poxviruses, and other known viruses in the art, as well as plasmids, cosmids and phages, etc. Many publications well-known in the art discuss the use of a variety of such vectors for delivery of genes. See, e.g., Ausubel et al., supra; Kay, M A. et al., 2001, *Nat. Med.*, 7:33-40; and Walther W et al., 2000, *Drugs* 60:249-71).

Methods for assembly of the recombinant vectors are well-known. See, for example, WO 00/15822 and other references cited therein, all of which are incorporated by reference.

There are advantages and disadvantages to the various viral vector systems. The limits of how much DNA can be packaged is one determinant in choosing which system to employ. rAAV tend to be limited to about 4.5 kb of DNA, whereas lentivirus (e.g., retrovirus) system can accommodate 4-5 kb.

AAV Vectors

Adeno-associated viruses are small, single-stranded DNA viruses which require a helper virus for efficient replication (Berns, K I, *Parvoviridae: the viruses and their replication*, p. 1007-1041 (vol. 2), in Fields, B N et al., *Fundamental Virology*, 3rd Ed., (Lippincott-Raven Publishers, Philadelphia (1995)). The 4.7 kb genome of AAV has two inverted terminal repeats (ITR) and two open reading frames (ORFs) which encode the Rep proteins and Cap proteins, respectively. The Rep reading frame encodes four proteins of molecular weights 78, 68, 52 and 40 kDa. These proteins primarily function in regulating AAV replication and rescue and integration of the AAV into the host cell chromosomes. The Cap reading frame encodes three structural proteins of molecular weights 85 (VP 1), 72 (VP2) and 61 (VP3) kDa which form the virion capsid (Berns, supra). VP3 comprises >80% of total AAV virion proteins.

Flanking the rep and cap ORFs at the 5' and 3' ends are 145 by ITRs, the first 125 bp's of which can form Y- or T-shaped duplex structures. The two ITRs are the only cis elements essential for AAV replication, rescue, packaging and integration of the genome. Two conformations of AAV ITRs called "flip" and "flop" exist (Snyder, R O et al., 1993, *J Virol.*, 67:6096-6104; Berns, K I, 1990 *Microbiol Rev,* 54:316-29). The entire rep and cap domains can be excised and replaced with a transgene such as a reporter or therapeutic transgene (Carter, B J, in *Handbook of Parvoviruses*, P. Tijsser, ed., CRC Press, pp. 155-168 (1990)).

AAVs have been found in many animal species, including primates, canine, fowl and human (Murphy, F A et al., *The Classification and Nomenclature of Viruses: Sixth Rept of the Int'l Comme on Taxonomy of Viruses, Arch Virol*, Springer-Verlag, 1995). Six primate serotypes are known (AAV1, AAV2, AAV3, AAV4, AAV5 and AAV6).

The AAV ITR sequences and other AAV sequences employed in generating minigenes, vectors, and capsids, and other constructs that are used in the present invention may be obtained from a variety of sources. For example, the sequences may be provided by any of the above 6 AAV serotypes or other AAV serotypes or other densoviruses, including both presently known human AAV and yet to yet-to-be-identified serotypes. Similarly, AAVs known to infect other animal species may be the source of ITRs used in the present molecules and constructs. Capsids from a variety of serotypes of AAV may be combined in various mixtures with the other vector components (e.g., WO2001/83692 incorporated by reference). Many of these viral strains or serotypes are available from the American Type Culture Collection (ATCC), Manassas, Va., or are available from a variety of other sources (academic or commercial).

It may be desirable to synthesize sequences used in preparing the vectors and viruses of the invention using known techniques, based on published AAV sequences, e.g., available from a variety of databases. The source of the sequences utilized to prepare the present constructs is not considered to be limiting. Similarly, the selection of the AAV serotype and species (of origin) is within the skill of the art and is not considered limiting The Minigene As used herein, the AAV sequences are typically in the form of a rAAV construct (e.g., a minigene or cassette) which is packaged into a rAAV virion. At minimum, the rAAV minigene is formed by AAV ITRs and a heterologous nucleic acid molecule for delivery to a host cell. Most suitably, the minigene comprises ITRs located 5' and 3' to the heterologous sequence. However, minigene comprising 5' ITR and 3' ITR sequences arranged in tandem, e.g., 5' to 3' or a head-to-tail, or in another configuration may also be desirable. Other embodiments include a minigene with multiple copies of the ITRs, or one in which 5' ITRs (or conversely, 3' ITRs) are located both 5' and 3' to the heterologous sequence. The ITRs sequences may be located immediately upstream and/or downstream of the heterologous sequence; intervening sequences may be present. The ITRs may be from AAV5, or from any other AAV serotype. A minigene may include 5' ITRs from one serotype and 3' ITRs from another.

The AAV sequences used are preferably the 145 by cis-acting 5' and 3' ITR sequences (e.g., Carter, B J, supra). Preferably, the entire ITR sequence is used, although minor modifications are permissible. Methods for modifying these ITR sequences are well-known (e.g., Sambrook, J. et al., *Molecular Cloning: A Laboratory Manual*, 3$^{rd}$ Edition, Cold Spring Harbor Press, Cold Spring Harbor, N.Y., 2001; Brent, R et al., eds., *Current Protocols in Molecular Biology*, John Wiley & Sons, Inc., 2003; Ausubel, F M et al., supra; Carter et al., supra; and Fisher, K et al., 1996 *J Virol.* 70:520-32). It is conventional to engineer the rAAV virus using known methods (e.g., Bennett, J et al. 1999, supra). An example of such a molecule employed in the present invention is a "cis-acting" plasmid containing the heterologous sequence, preferably the Chop2 sequence, flanked by the 5' and 3' AAV ITR sequences.

The heterologous sequence encodes a protein or polypeptide which is desired to be delivered to and expressed in a cell. The present invention is directed to hGM-CSF sequences under the control of a selected promoter and other conventional vector regulatory components.

The Transgene being Targeted and Expressed

In a most preferred embodiment, the heterologous sequence is a nucleic acid molecule that functions as a transgene. The term "transgene" as used herein refers to a nucleic acid sequence heterologous to the AAV sequence, and encoding a desired product, preferably hGM-CSF and regulatory sequences which direct or modulate transcription and/or translation of this nucleic acid in a host cell, enabling expression in such cells of the encoded product (in vitro or in vivo). Preferred polypeptide products are those that can be delivered to the lungs, particularly to AM.

The transgene is delivered and expressed in order to prevent or treat or otherwise improve the status of a subject with an influenza infection.

Using an mGluR6 promoter operatively linked to a hGM-CSF coding sequence and a reporter gene, e.g., GFP or another fluorescent protein, an insert of about 4.5 kb is preferred—1 kb for the GM-CSF, 0.7 kb for the reporter, 10 kb—for the mGluR6 promoter region and about 0.4 kb for conventional transcriptional regulatory factors.

Different transgenes may be used to encode separate subunits of the protein being delivered, or to encode different polypeptides the co-expression of which is desired. If a single transgene includes DNA encoding each of several subunits, the DNA encoding each subunit may be separated by an internal ribozyme entry site (IRES), which is preferred for short subunit-encoding DNA sequences (e.g., total DNA, including IRES is <5kB). Other methods which do not employ an IRES may be used for co-expression, e.g., the use of a second internal promoter, an alternative splice signal, a co- or post-translational proteolytic cleavage strategy, etc., all of which are known in the art.

The coding sequence or non-coding sequence of the nucleic acids useful herein preferably are codon-optimized for the species in which they are to be expressed, most particularly, humans Such codon-optimization is routine in the art.

While a preferred transgene encodes a full length polypeptide, preferably hGM-CSF (SEQ ID NO:4, as indicated, the present invention is also directed to vectors that encode a biologically active fragment or a conservative amino acid substitution variant of hGM-CSF (or other polypeptide of the invention to be delivered to or expressed in lungs.

The fragment or variant is expressed by targets cells in the subject being transformed with hGM-CSF and is able to endow such cells with influenza-resistance that is functionally equivalent to that of the full length or substantially full length polypeptide having a native, rather than variant, amino acid sequence. A biologically active fragment or variant is a "functional equivalent"—a term that is well understood in the art and is further defined in detail herein. The requisite biological activity of the fragment or variant, using any method disclosed herein or known in the art has the following activity relative to the wild-type native polypeptide: about 50%, about 55%, about 60%, about 65%, about 70%, about 75%, about 80%, about 85%, about 90%, about 95%, about 99%, and any range derivable therein, such as, for example, from about 70% to about 80%, and more preferably from about 81% to about 90%; or even more preferably, from about 91% to about 99%.

It should be appreciated that any variations in the coding sequences of the present nucleic acids and vectors that, as a result of the degeneracy of the genetic code, express a polypeptide of the same sequence, are included within the scope of this invention.

The amino acid sequence identity of the variants of the present invention are determined using standard methods, typically based on certain mathematical algorithms. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the WWW web address gcg.com, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (*CABIOS* 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) *J. Mol. Biol.* 215:403-10). BLAST nucleotide searches can be performed with the NBLAST program, score=100, wordlength=12 to obtain nucleotide sequences homologous to, e.g., DAN encoding Chop2 of *C. reinhardtii*. BLAST protein searches can be performed with the XBLAST program, score=50, wordlength=3 to obtain amino acid sequences homologous to the appropriate reference protein such as Chop2. To obtain gapped alignments for comparison purposes, Gapped BLAST can be utilized (Altschul et al. (1997) Nucleic Acids Res. 25:3389-3402). When utilizing BLAST and Gapped BLAST programs, the default parameters of the respective programs (e.g., XBLAST and NBLAST) can be used. See World Wide Web URL ncbi.nlm.nih.gov.

The preferred amino acid sequence variant has the following degrees of sequence identity with the native, full length hGM-CSF (SEQ ID NO:4) about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, from about 70% to about 80%, and more preferably from about 81% to about 90%; or even more preferably, from about 91% to about 99% identity.

Any of a number of known recombinant methods are used to produce a DNA molecule encoding the polypeptide fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, *DNA* 2:183-93). These mutations include simple deletions or insertions, systematic deletions, insertions or substitutions of clusters of bases or substitutions of single bases.

Regulatory Sequences

The minigene or transgene of the present invention includes appropriate sequences operably linked to the coding sequence or ORF to promote its expression in a targeted host cell. "Operably linked" sequences include both expression control sequences such as. promoters that are contiguous with the coding sequences and expression control sequences that act in trans or distally to control the expression of the polypeptide product.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance protein processing and/or secretion. Many varied expression control sequences, including native and non-native, constitutive, inducible and/or tissue-specific, are known in the art and may be utilized herein. depending upon the type of expression desired.

Expression control sequences for eukaryotic cells typically include a promoter, an enhancer, such as one derived from an immunoglobulin gene, SV40, CMV, etc., and a polyadenylation sequence which may include splice donor and acceptor sites. The polyadenylation sequence generally is inserted 3' to the coding sequence and 5' to the 3' ITR sequence. PolyA from bovine growth hormone is a suitable sequence.

The regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element. (See, for example, Wang L and Verma, I, 1999, *Proc Nat'l Acad Sci USA*, 96:3906-10).

An IRES sequence, or other suitable system as discussed above, may be used to produce more than one polypeptide from a single transcript. n exemplary IRES is the poliovirus IRES which supports transgene expression in photoreceptors, RPE and ganglion cells. Preferably, the IRES is located 3' to the coding sequence in the rAAV vector.

The promoter may be selected from a number of constitutive or inducible promoters that can drive expression of the selected transgene in an ocular setting, preferably in retinal neurons. A preferred promoter is "cell-specific", meaning that it is selected to direct expression of the selected transgene in a particular ocular cell type, such as photoreceptor cells.

Examples of useful constitutive promoters include the exemplified ??? CMV immediate early enhancer/chicken β-actin (CβA) promoter-exon 1-intron 1 element, the RSV LTR promoter/enhancer, the SV40 promoter, the CMV promoter, the dihydrofolate reductase (DHFR) promoter, and the phosphoglycerol kinase (PGK) promoter.

It is envisioned that minor sequence variations in the various promoters and promoter regions discussed herein—whether additions, deletions or mutations, whether naturally occurring or introduced in vitro, will not affect their ability to drive expression in the cellular targets of the present invention. Furthermore, the use of other promoters, even if not yet discovered, that are characterized by abundant and/or specific expression in retinal cells, particularly in bipolar or ganglion cells, is specifically included within the scope of this invention.

An inducible promoter is used to control the amount and timing of production of the transgene product in an ocular cell. Such promoters can be useful if the gene product has some undesired, e.g., toxic, effects in the cell if it accumulates excessively. Inducible promoters include those known in the art, such as the Zn-inducible sheep metallothionine (MT) promoter, the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any inducible promoter the action of which is tightly regulated and is specific for the particular target ocular cell type, may be used. Other useful types of inducible promoters are ones regulated by a specific physiological state, e.g., temperature, acute phase, a cell's replicating or differentiation state.

Selection of the various vector and regulatory elements for use herein are conventional, well-described, and readily available. See, e.g., Sambrook et al., supra; and Ausubel et al., supra. It will be readily appreciated that not all vectors and expression control sequences will function equally well to express the transgene, preferably hGM-CSF. Clearly, the skilled artisan may apply routine selection among the known expression control sequences without departing from the scope of this invention and based upon general knowledge as well as the guidance provided herein. One skilled in the art can select one or more expression control sequences, operably link them to the coding sequence being expressed to make a minigene, insert the minigene or vector into an AAV vector, and cause packaging of the vector into infectious particles or virions following one of the known packaging methods for rAAV.

In Vitro Testing of Polypeptides

A polypeptides or peptide to be used in this invention may be tested for binding activity or their biological activity any one of the assays described and/or exemplified herein. The binding is preferably tested in a competition assay in which the polypeptide being tested is incubated with appropriate concentrations of GM-CSF-R protein (see above) or GM-CSF-R-bearing cells or membrane preparations and native GM-CSF, and the binding of the GM-CSF is measured in the presence vs. absence of the test polypeptide. Any other appropriate binding assays known in the art may be used.

The biological activity of a polypeptide or peptide of the invention may be determined in in vitro colony forming assays, for example, as disclosed in Lee F et al., *Proc. Natl. Acad. Sci. USA* 82:4360-64, 1985. (See also, Rennick, D M et al., *J. Immunol.* 134: 910-14, 1985.) Briefly, colony-forming assays are performed with either human bone marrow cells obtained from patients with nonhematologic disease or with human cord blood cells (Knudtzon, S., *Blood* 43, 357-61, 1974; Ogawa, M et al. *Proc. Natl Acad. Sci. USA* 80:4494-98, 1983). Approximately $10^5$ nonadherent cells from bone marrow or cord blood were added to 35-mm Petri dishes in a total volume of 1 ml of modified Iscove's medium (Rennick, D M et al., *J. Immunol.* 134:910-14, 1985) supplemented with 0.9% methylcellulose containing the test sample at a concentration not greater than 30% of the total volume. Cultures were incubated for 3 days, then 1 unit of human erythropoietin was added. Colonies were counted after 10-14 days. The cellular composition of colonies was determined after applying individual colonies to glass slides and staining with Wright-Giemsa stain.

In Vivo Testing of Polypeptides

The ability of a test polypeptide (such as a functional variant of hGM-CSF) to inhibit or prevent influenza infection and its lethal effects is described in the Examples below. Other tests known in the art that measure the same type of activity may also be used. Also included are tests of conjugated GM-CSF or functional variants or derivatives thereof described herein where the GM-CSF is conjugated to polyethylene glycol or to nanoparticles (NP), preferably lipid NP.

Method of Preventing or Treating Influenza Infection

The hGM-CSF or functional variants thereof are used in method to prevent, attenuate infection by influenza virus, or to induce inflammatory responses in the lung that would achieve the same effect in vitro or in vivo, and to treat infections and subsequent pulmonary or other events.

The polypeptides/peptides that may be employed in the pharmaceutical compositions of the invention include the polypeptide compounds described above, as well as, where appropriate, the pharmaceutically acceptable salts thereof. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to stimulate colony formation of human BM cells and are exploited in the treatment of, for example, acute influenza infection.

The compounds of the invention may be incorporated into convenient dosage forms, most preferably injectable or inhalable preparations. Solid, semi-solid or liquid pharmaceutically acceptable carriers may be employed.

Liquid carriers may include saline, water, dextrose, glycerol and the like. Similarly, the carrier or diluent may include any prolonged release material, such as glyceryl monostearate or glyceryl distearate. When a liquid carrier is used, the preparation may be in the form of a sterile injectable liquid (e.g., a solution), or an aqueous or nonaqueous liquid suspension. A summary of such pharmaceutical compositions may be found, for example, in Gennaro, A R, *Remington: The Science and Practice of Pharmacy*, Lippincott Williams & Wilkins Publishers; $21^{St}$ Ed, 2005 (or later edition).

In some embodiments, a nebulizer is used to deliver the pharmaceutical composition of the invention to the lung. Nebulizers create aerosols from liquid drug formulations by using, for example, ultrasonic energy to form fine particles that may be readily inhaled (see, e.g., Verschoyle et al., *Brit. J. Cancer,* 1999, 80(Suppl. 2): 96. Examples of nebulizers include devices supplied by Sheffield/Systemic Pulmonary Delivery Ltd. (See, Armer et al., U.S. Pat. No. 5,954,047; van der Linden et al., U.S. Pat. Nos. 5,950,619 and 5,970,974) and Batelle Pulmonary Therapeutics (Columbus, Ohio). In other embodiments, an electrohydrodynamic ("EHD") aerosol device is used for delivery to the lung. EHD aerosol devices use electrical energy to aerosolize liquid drug solutions or suspensions. See e.g., Noakes et al., U.S. Pat. No. 4,765,539). EHD aerosol devices may more efficiently deliver drugs to the lung than other pulmonary delivery technologies.

The pharmaceutical preparations are made following conventional techniques of pharmaceutical chemistry, as appropriate, to give the desired products for oral, parenteral, topical, intranasal, intrabronchial, and rectal administration. The pharmaceutical compositions may also contain minor amounts of nontoxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, most preferably humans.

The term "systemic administration" refers to administration of a composition or agent such as the polypeptide described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as instillation in the lung, preferably via intranasal deliver as the preferred route, or intraperitoneal, or to a specific organ. Other examples include intrabronchial, etc. The term "local administration" refers to administration of a composition or drug into a limited, or circumscribed, anatomic space, such as subcutaneous (s.c.) injections, intramuscular (i.m.) injections. One of skill in the art would understand that local administration or regional administration often also result in entry of a composition into the circulatory system, i.e., so that s.c. or i.m. are also routes for systemic administration.

Instillable, injectable or infusible preparations can be prepared in conventional forms, either as solutions or suspensions, solid forms suitable for solution or suspension in liquid prior to injection or infusion, or as emulsions. Though the preferred routes of administration are regional (into the lungs), the pharmaceutical composition may be administered systemically or topically or transdermally.

Other pharmaceutically acceptable carriers for compositions of the present invention are liposomes, pharmaceutical compositions in which the active polypeptide is contained either dispersed or variously present in corpuscles consisting of aqueous concentric layers adherent to lipidic layers. The active polypeptide is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Thus, in a preferred embodiment, the GM-CSF or variant/derivative is conjugated to polyethylene glycols (PEG) or "PEGylated." PEGylation is the process of covalent attachment of PEG polymer chains to another molecule and is routinely achieved by incubation of a reactive derivative of PEG with the target macromolecule. Among other things, covalent attachment of PEG to a therapeutic protein can "mask" the agent from the host's immune system and increase the hydrodynamic size (size in solution) of the agent which prolongs its circulatory time by reducing renal clearance. PEGylation can also provide water solubility to hydrophobic proteins. PEG monomers can be bonded to GM-CSF at up to 12 sites (at any of 11 Lys residues and the N-terminal amino group, preferably by random PEGylation. If PEGylation at multiple sites adversely affects bioactivity, PEGylation can be done in a site-directed manner at the single glycosylated site on (yeast-derived) GM-CSF. Recombinant GM-CSF, preferably hGM-CSF produced in yeast is a preferred target for directed and controlled PEGylation.

In another embodiment the GM-CSF or variant/derivative is conjugated to or otherwise inserted into lipid nanoparticles (NP). Preferably, rGM-CSF is conjugated to NP larger than 10 nm (based on the size of human serum albumin being 10 nm) by using standard chemistries, such as with EDC (N-ethyl-N'-dimethylaminopropyl-carbodiimide). This will couple reactive PEGs (e.g., methoxyl PEG hydrazide) or other NP of discrete known sizes directly or indirectly to the GM-CSF. These conjugated materials are then preferably subjected to gel filtration and fractionation (FPLC, SUPEROSE® 6 HR 10/30, etc.) to generate a defined size or limited size distribution. PEGylated GM-CSF may comprised from 1 to 12 PEG monomers bonded to each GM-CSF molecule, with 12 mers being preferred.

NP are particles with a diameter from about 5 nm to up to about 1000 nm. The term "nanoparticles" as it is used herein refers to particles formed by a polymeric matrix in which the active compound is dispersed, also known as "nanospheres", and also refers to NP which are composed of a core containing the active compound which is surrounded by a polymeric membrane, also known as "nanocapsules". Alternatively, the active compounds may be chemically bonded to or conjugated to the NP. In certain embodiments, NP are preferred having a diameter from about 10 nm to about 500 nm, more preferably from about 10 nm to about 200 nm.

NP can be prepared by in situ polymerization of dispersed monomers or by using preformed polymers. Since polymers prepared in situ are often not biodegradable and/or contain toxic byproducts, NP from preformed polymers are preferred. NP from preformed polymers can be prepared by different techniques, e.g., by emulsion evaporation, solvent displacement, salting-out, mechanical grinding, microprecipitation, and by emulsification diffusion. With the methods described above, NP can be formed with various types of polymers. For use in the present methods, NP made from biocompatible polymers are preferred. "Biocompatible" refers to material that after introduction into a biological environment has no serious deleterious effects on that environment. The term "biodegradable" refers to material that after introduction into a biological environment is enzymatically or chemically degraded into smaller molecules, which can subsequently be eliminated. Examples are polyesters from hydroxycarboxylic acids such as polylactic acid (PLA), polyglycolic acid (PGA), polycaprolactone (PCL), copolymers of lactic acid and glycolic acid (PLGA), copolymers of lactic acid and caprolactone, poly-$\epsilon$-caprolactone, polyhydroxybutyric acid and poly(ortho)esters, polyurethanes, polyanhydrides, polyacetals, polydihydropyrans, polycyanoacrylates, natural polymers such as alginate and other polysaccharides including dextran and cellulose, collagen and albumin. Further description of preparing nanoparticles can be found, for example, in U.S. Pat. No. 6,264,922, particularly with respect to nebulized aerosols with NP dispersions. See also WO2007-115134A1

The GM-CSF or variant/derivative can be conjugated to other nanomaterials such as dendrimers/dendritic polymers (which terms are used interchangeably). Preferably, the core molecule of the dendrimer is a naturally occurring amino acid such as Lys so that it can be properly metabolized. Dendritic poly-Lys may be built from a Gly linker originally joined through a benzyl linker to a resin. Other linkers such as Ala can be employed or the linker may be omitted. Non-natural amino acids, even if not α-amino acids, can be employed. The amino acids used in building the core molecule can be in either the D or L-form. More details about the chemistry and pharmaceutical use of dendritic polymers can be found in Tomalia D A et al., *Biochem Soc Trans.* 35:61-7, 2007; Braun C S et al., *J Pharm Sci.* 94:423-36, 2005; Svenson S et al., *Adv Drug Deliv Rev.* 57:2106-29, 2005; and U.S. Pat. Nos. 4,289,872; 4,558,120; 4,376,861; 4,568,737; 4,507,466; 4,587,329; 4,515,920; 4,599,400; 4,517,122; and 4,600,535.

Suitable surface modifiers for use with liposomes and NP can selected from known organic and inorganic pharmaceutical excipients, including various polymers, low molecular weight oligomers, natural products and surfactants. Surface modifiers include nonionic and ionic surfactants. Representative examples include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tween, polyethylene glycols (as discussed herein in more detail), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients. See, for example, R. C. Rowe, et al., eds, *Handbook of Pharmaceutical Excipients*, 5$^{th}$ Ed. (American Pharmaceutical Association Publications, 2005; or later edition).

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

Therapeutic Methods

The methods of this invention are used to prevent, attenuate or otherwise treat influenza infection in a subject in need thereof, by, for example, stimulating AM's to limit virus infection or spread. The active polypeptide or variant is preferably administered in the form of a pharmaceutical composition as described above.

Doses of polypeptides preferably include pharmaceutical dosage units comprising an effective amount of the polypeptide. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a regional concentration or a steady state concentration in vivo which results in a measurable reduction in any relevant parameter of disease.

The amount of active compound to be administered depends on the particular polypeptide or variant selected, the precise disease or condition, the route of administration, the health and weight of the recipient, the existence of other concurrent treatment, if any, the frequency of treatment, the nature of the effect desired, and the judgment of the skilled practitioner.

A preferred single dose, given once daily for treating a subject, preferably a mammal, more preferably human who his suffering from or susceptible to influenza infection is between about 10 μg/kg and about 20 mg/kg, preferably between about 1 mg/kg and about 5 mg/kg, for example, via instillation (by inhalation). Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

An effective concentration of the polypeptide for to be achieved in vivo is in the range of about 0.5 nM to about 1 μM, more preferably from about 2 nM to about 100 nM. Effective doses and optimal dose ranges may be determined in vitro using the methods described herein.

Having now generally described the invention, the same will be more readily understood through reference to the following examples which are provided by way of illustration, and are not intended to be limiting of the present invention, unless specified. The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Materials and Methods

Mice. WT C57BL/6 mice were purchased from the National Cancer Institute. Tg mice overexpressing GM-CSF in alveolar epithelial type II cells were generated from GM$^{-/-}$ mice on a C57BL/6 background, by expression of a chimeric gene containing GM-CSF under the control of the human SP-C promoter (SPC-GM) (24). These SPC-GM mice were backcrossed to C57BL/6 mice for >10 generations, and DNA typing confirmed that they had the genetic markers of C57BL/6 mice. Experiments were conducted under guidelines of the Institutional Animal Care and Use Committee at the University of Texas Health Science Center at Tyler.

DNA Plasmids and in vivo Transfection. A DNA plasmid that expresses murine GM-CSF, pORF9-mGMCSF, and a control plasmid, pORF9-mcs (both from InvivoGen), were used to transform *Escherichia coli*, which was grown overnight in LB medium with ampicillin. Plasmid DNA was extracted, using the EndoFree Plasmid Giga Kit (QIAGEN). DNA was mixed with in vivo-JetPEI™ (Genesee Scientific, San Diego, Calif.), according to the manufacturer's instructions, and each mouse received 100 μg of this mixture by retro-orbital injection.

Influenza A Virus Infection. Eight-12 week-old mice were intranasally inoculated with 50 μl of PBS containing the H1N1 PR8 strain (Charles River), the H1N1 mouse-adapted swine influenza strain, California/04/09 (25) or the H3N2 HK68 strain.

Intranasal Treatment with GM-CSF. Wild-type (WT) mice were treated intranasally daily with 1.34 mg/kg recombinant murine GM-CSF (Invitrogen) for 7 days, prior to infection with PR8 H1N1 influenza.

DNA Plasmids and in vivo Transfection. DNA was obtained from a plasmid that expresses murine GM-CSF, mixed with IN VIVO-JETPEI® -(Genesee Scientific, San Diego, Calif.), and administered by retro-orbital injection.

Flow Cytometry. Cells were stained with monoclonal antibodies to murine CD11b (Mac-1a), CD11c (HL3), CD3 (145-2C11), CD4 (L3T4), CD8a (53-6.7), CD8a (Ly-2), CD45 (Ly5), major histocompatibility complex class II (I-A/I-E), F4/80 (BM8), Fas (15A7) and Annexin V (all from eBioscience). Control cells were unstained or stained with isotype control antibodies. For surface staining, isolated cells (10$^6$) were stained with antibodies, and then washed with 1 ml of staining buffer. For intracellular staining, cells were permeabilized in a fixation/permeabilization working solution for 1 hour at 4° C. in the dark, and washed with permeabilization buffer. Washed cells were stained with antibodies and washed again. All flow cytometry data were acquired on a BD FACS Calibur (BD, San Jose, Calif.) and analyzed using FlowJo software (TreeStar, Inc).

Animal Irradiation. SPC-GM mice were subjected to whole-body irradiation (450 rads), using a J.L. Shepherd CS-137 irradiator Model 143.

Depletion of Neutrophils, T Cells and B Cells. Peripheral T cells or CD8+ T cells or CD4+ T cells were depleted, respectively, with mAbs to Thy-1.2 (30H12), CD8a (53.6.72), CD4 (GK1.5) (BioXCell, West Lebanon, N.H.). Mice were given 200-500 μg of antibody (or rat IgG2a or IgG2b isotype controls) intraperitoneally at −3, 0 and 3 days post-influenza infection. For B cell depletion, mouse anti-CD22 mAb conjugated to N-acetyl-γ-calicheamicin dimethylhydrazide ("CD22/cal," Pfizer Research, Cambridge, Mass.) was used. SPC-GM mice were given 160 μg/kg/injection anti-CD22/cal intraperitoneally or an anti-rat mAb that does not bind to mouse cells, conjugated to calicheamicin (GG5/cal, Pfizer), as a control, 10 and 5 days before influenza infection. To deplete neutrophils, SPC-GM mice were treated with anti-GR1 mAb (RB6-8C5, BD Pharmingen), 100 μg intraperitoneally and 100 μg intranasally, 1 day prior to infection, and 3 and 6 days after infection. Control SPC-GM mice were treated with isotype control rat IgG2b. Depletion of alveolar phagocytes. SPC-GM mice were given 90 μl of clodronate-liposome intranasally to deplete alveolar phagocytes or 90 μl of PBS-liposome as controls, either 1 day before, or 1-6 days after influenza infection. Clodronate- and PBS-liposome were obtained from the VU University Amsterdam, the Netherlands (See the Worldwide web URL clonodrateliposomes-dot-org).

Viral Quantitation. Madin-Darby Canine Kidney (MDCK) cells were cultured in 96-well-plates with complete medium containing MEM, 10% FBS, 0.1 mM non-essential amino acids, and 1.0 mM sodium pyruvate overnight. The next day, lung homogenates were serially diluted 10-fold with MEM and loaded on confluent MDCK cells. After 1 hour, samples were washed with Hanks' buffer and cultured in medium containing MEM, 0.1% BSA, 0.5 μg/ml TPCK-trypsin, 100 U/ml of penicillin and 100 μg/ml streptomycin at 37° C. and 5% $CO_2$. Seventy-two hours post-infection, cellular pathologic changes were quantified under a microscope, and the 50% tissue culture infective dose ($TCID_{50}$) was calculated by the Spearman-Karber formula.

To quantify viral RNA, total RNA was extracted from 100 μl of lung homogenate, reverse transcribed to cDNA using random primers and superscript II (Invitrogen), and real-time polymerase chain reaction (PCR) was performed with influenza virus-specific primers and probes, using a 7300 Real-Time PCR System (Applied Biosystems).

Histopathology. Lung tissue from SPC-GM and wild-type mice was fixed in 10% neutral buffered formalin and embedded in paraffin. Five μm sections were made, stained with hematoxylin and eosin, and evaluated under an Olympus DP70 microscope.

Measurement of Cytokines. Mouse lungs were mechanically homogenized in 1 ml PBS on ice, and centrifuged at 3500 rpm for 10 min at 4° C. Supernatants were collected, and levels of tumor necrosis factor-α, monocyte chemoattractant protein-1, interleukin-6, interleukin-10, interferon-α and interferon-γ in the supernatants were measured by EIA (all from eBioscience).

Phagocytosis Assays. Macrophage phagocytosis in vivo was evaluated by intranasal administration of fluorescein isothiocyanate (FITC)-labeled influenza A PR8 virus, as previously described (26). Briefly, purified virus stocks were incubated with FITC (10:1 mixture, v/v) for 1 h, followed by centrifugation with a 30 kD ultracentrifuge filters (Millipore) to remove unlabeled FITC. The FITC-labeled PR8 H1N1 was administered intranasally to mice. Two hours later, AM from BAL fluid were stained with allophycocyanin anti-F4/80, washed in staining buffer, and Trypan blue was added to quench fluorescence of extracellular FITC. Cell-associated fluorescence was measured by flow cytometry. FITC stock in PBS was given intranasally to mice as a control.

To quantify macrophage phagocytosis of beads in vitro, AMs were collected from BAL fluid from naive SPC-GM and WT mice, and $3 \times 10^5$ AM were incubated with $3.64 \times 10^7$/ml of 1.0 μm yellow-green FLUOSPHERES® Carboxylate-Modified beads (Invitrogen) in 100 μl of RPMI-1640 medium containing 0.1% bovine serum albumin at 37° C. for 30 min. AMs were then washed and stained with antibodies to F4/80 at 4° C. for 30 min, then analyzed by flow cytometry.

Evaluation of Apoptosis. AMs were collected by centrifugation of BAL fluid from mice infected with $5 \times LD_{50}$ of PR8 virus, and stained with allophycocyanin-anti-mouse F4/80, with or without phycoerythrin-anti-Fas or FITC-annexin V, and results were analyzed by flow cytometry. To evaluate apoptosis in vitro, AM were obtained from BAL fluid of naive mice and infected with influenza virus PR8 at a multiplicity of infection of 1 for 60 min at 37° C. Cells were then washed three times with fresh medium and maintained in MEM supplemented with 0.1% bovine serum albumin and 0.5 μg/ml TPCK-trypsin at 37° C. Eighteen hours later, cells were harvested, stained with allophycocyanin-anti-F4/80 and FITC-annexin V, and flow cytometry was performed Adoptive Transfer of Alveolar Cells. SPC-GM mice were depleted of alveolar phagocytes by treatment with clodronate-liposome, as above. Three days later, BAL cells (99% AM) from naïve SPC-GM mice were centrifuged at 300 g for 10 min, counted and resuspended in PBS at a concentration of $3.4 \times 10^7$ cells/ml. $2 \times 10^6$ cells in 60 μL were transferred intratracheally to alveolar phagocyte-depleted SPC-GM mice, which were infected intranasally with influenza virus 16 hours later.

EXAMPLE II

GM-CSF Expression in the Lung Reduces Mortality from Influenza

Figure 1B:
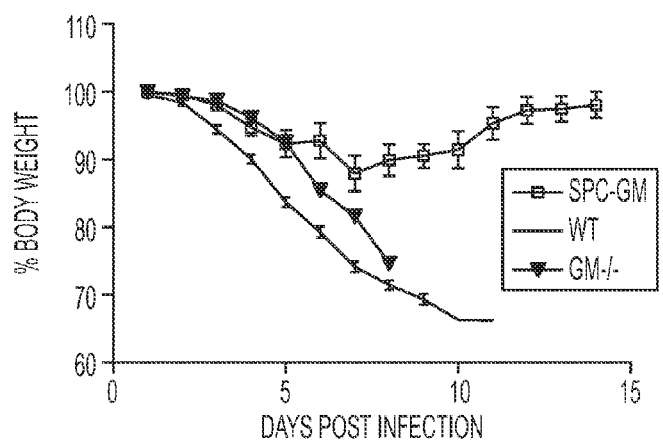

To determine if GM-CSF could protect against influenza, SPC-GM, GM−/− and WT mice were infected with 5 $LD_{50}$ of the influenza PR8 strain. All WT mice died after 8-11 days, and all GM−/− mice died after 6-8 days. In contrast, all SPC-GM mice, which only express GM-CSF in the lung, survived (FIG. 1A). WT and GM−/− mice progressively lost weight, whereas SPC-GM mice lost less weight and soon recovered (FIG. 1B). These results show that pulmonary expression of GM-CSF conferred marked protection against lethal influenza infection.

PR8 is a laboratory influenza strain. To determine if SPC-GM mice were resistant to clinical influenza strains, infected mice were infected with lethal doses of the H3N2 strain, HK68, and a mouse-adapted H1N1 California/04/092009 swine influenza pandemic strain (25). All WT mice died, whereas all the SPC-GM mice survived, indicating that GM-CSF in the lung protected against clinical and laboratory influenza strains (FIG. 1A).

EXAMPLE III

Delivery of GM-CSF to the Lungs of WT Mice Protects Against Influenza

Figure 1C:
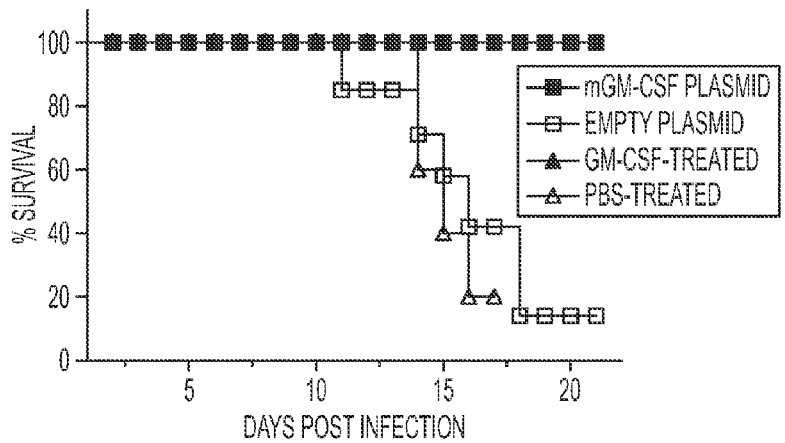

The studies in Example I suggested that GM-CSF produced in the lung protects against influenza. However, genetic differences other than GM-CSF production may have contributed to influenza resistance. To exclude this possibility, the effect of GM-CSF on WT mice was evaluated. A murine GM-CSF-expressing vector was coated with polyethyleneimine, which enhances DNA expression 400-fold and delivers it to the lung (27). All WT mice treated with this GM-CSF-expressing plasmid survived influenza infection, compared to no mice receiving the empty plasmid (FIG. 1C). Intranasal administration of recombinant mouse GM-CSF (rmGM-CSF) to WT mice also abrogated mortality from influenza (FIG. 1C).

EXAMPLE IV

Figure 2A:
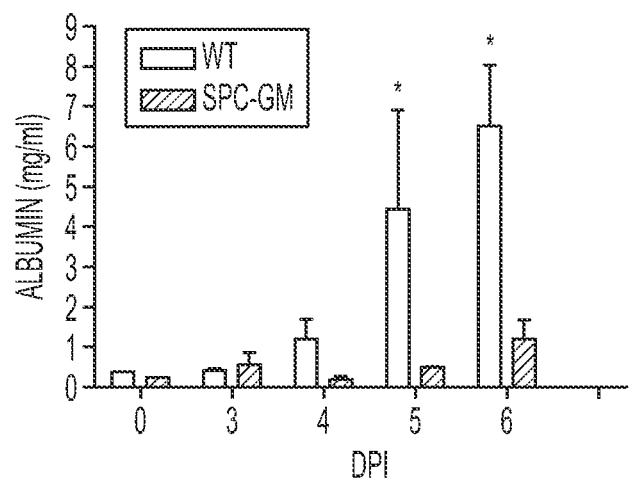
FIG. 2. Pulmonary GM-CSF Expression Reduces Lung Injury and Viral Burden, and Elicits Early Inflammation. (A) SPC-GM and WT mice (n=20/group) were infected with 5 $LD_{50}$ of influenza virus PR8. Three-6 days post-infection (DPI), 4-mice in each group were killed daily, and albumin levels in BAL fluid were measured by enzyme-linked immunoassay (EIA). Means±SEs are shown. * p=0.01, comparing SPC-GM and WT mice. (B) SPC-GM and WT mice (n=12/group) were infected with 5 $LD_{50}$ of PR8. One, 3 and 6 DPI, 4 mice in each group were killed, and viral loads were determined by measuring the $TCID_{50}$, as described in the Methods. * p=0.03, comparing SPC-GM and WT mice. (C) Histology of the lungs of SPC-GM and WT mice, both uninfected and 1-6 DPI with PR8. Representative sections, stained with hematoxylin and eosin, are shown, at 40× magnification. (D) Cytokine levels were measured by ELISA in lung homogenates from SPC-GM and WT mice, before and after infection with PR8 (n=3 per time point). Means±SEs are shown. * p<0.01, comparing SPC-GM and WT mice.
Figure 2B:
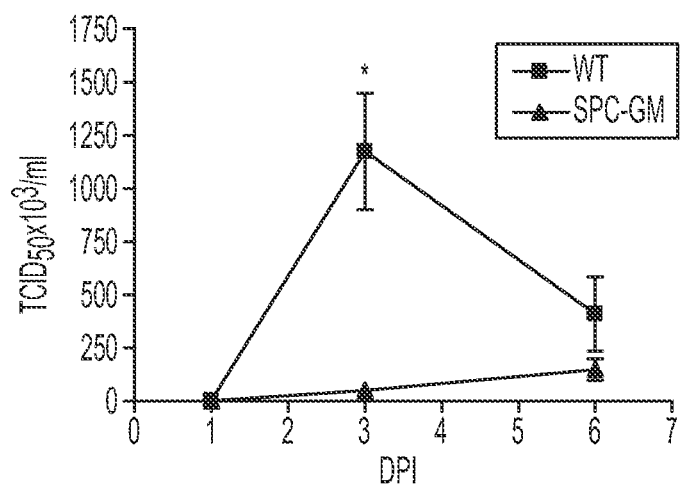

Effects of Pulmonary GM-CSF on Alveolar Injury, Viral Burden and Lung Inflammation After Influenza Infection To understand the mechanisms underlying the resistance of SPC-GM mice to influenza, the integrity of the alveolar barrier was assessed by measuring albumin levels in BAL fluid, which were similar in WT and SPC-GM mice before infection, but rose markedly in infected WT mice and were significantly higher than those in SPC-GM mice 5-6 days after infection (FIG. 2A). SPC-GM mice also had a lower viral burden, as the $TCID_{50}$ in lung homogenates was reduced 23-fold compared to WT mice, 3 days after infection (p=0.03, FIG. 2B).

Figure 2C:
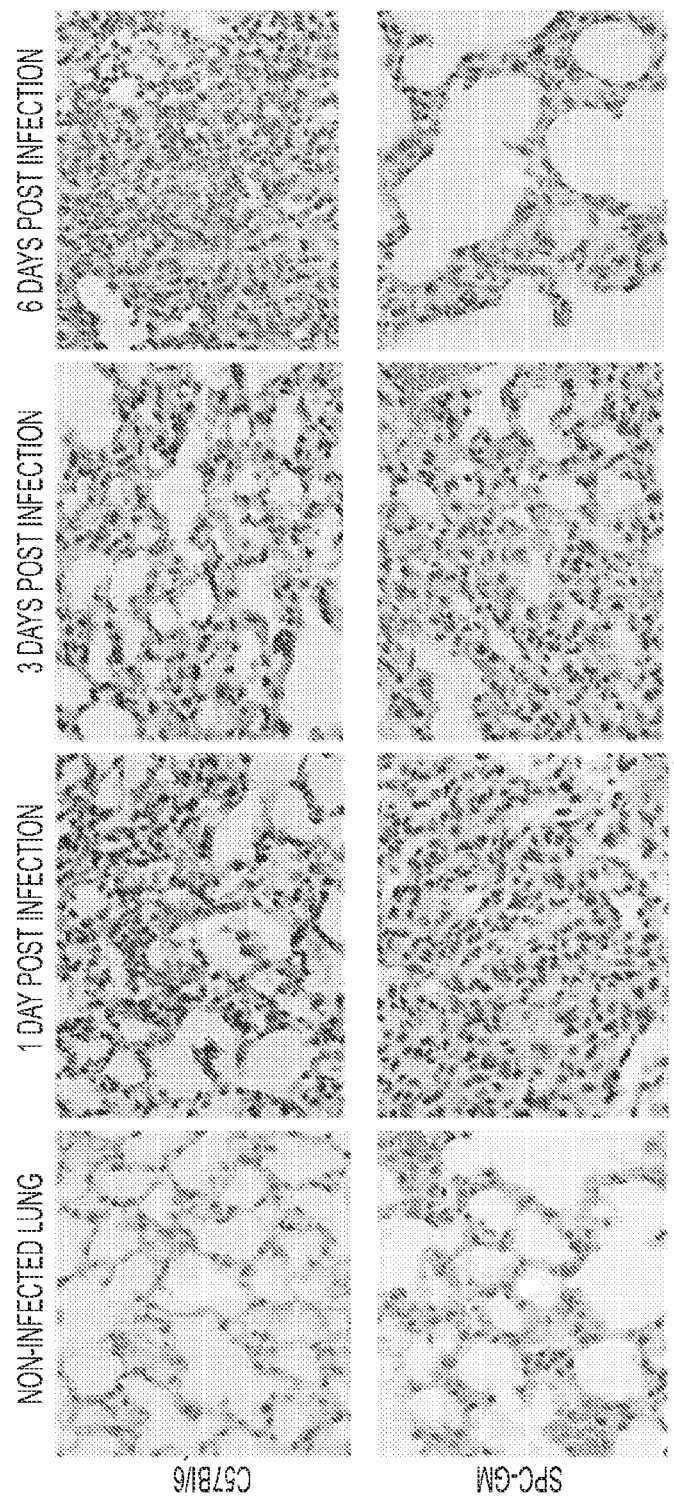

The pulmonary histopathology during influenza infection was evaluated. One day after infection, inflammation was much more marked in lungs of SPC-GM mice than in WT mice, with cellular infiltrates composed predominantly of lymphocytes and macrophages (FIG. 2C). By day 3 after infection, SPC-GM mice showed a more diffuse inflammatory mononuclear cell infiltrate, whereas WT mice showed a diffuse neutrophilic infiltrate. By day 6, inflammation was resolving in SPC-GM mice, while diffuse cellular infiltration persisted in WT mice, with almost no normal alveoli observed.

Figure 2D:
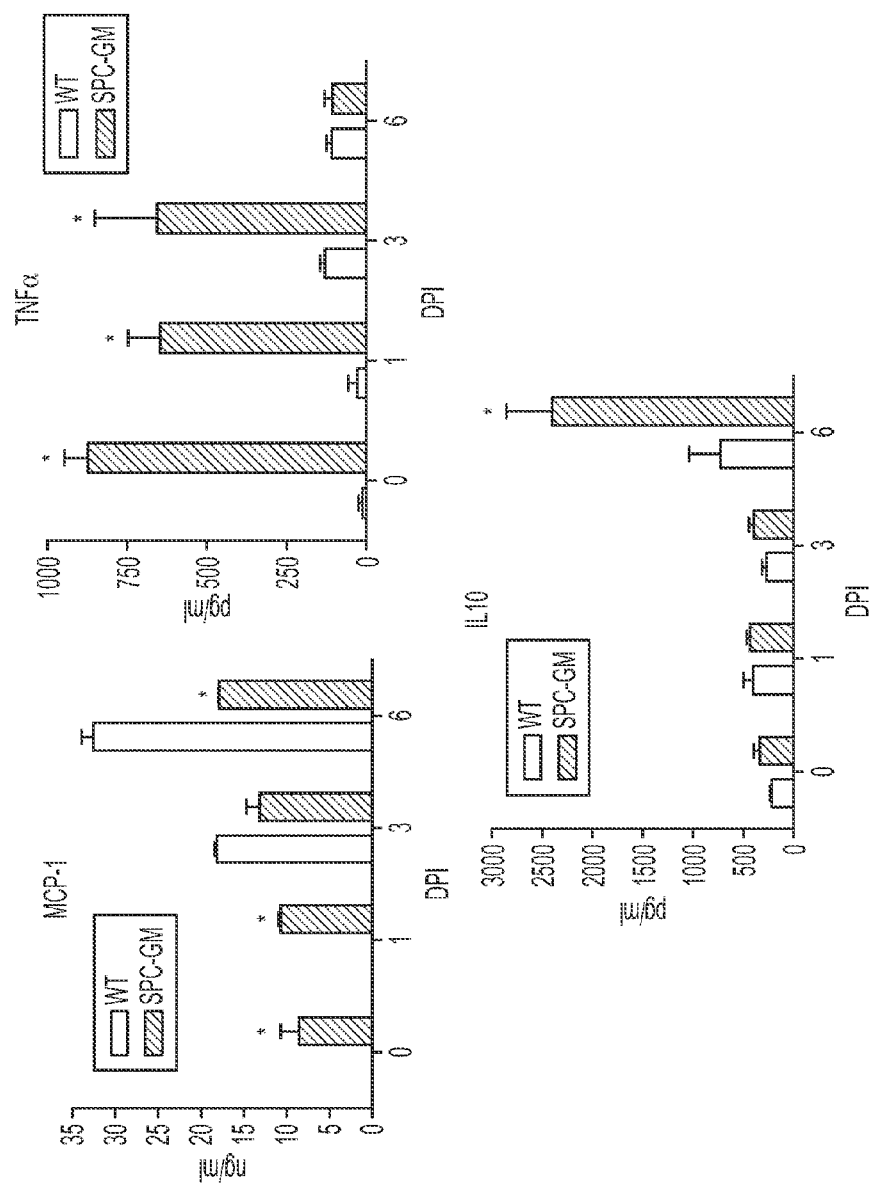

These histologic findings suggested that SPC-GM mice mount a rapid immune response to influenza infection. Concentrations of selected inflammatory cytokines were measured in lung homogenates. Surprisingly, naïve SPC-GM mice had high levels of monocyte chemoattractant protein (MCP)-1 and tumor necrosis factor (TNF)-α, compared to WT mice (FIG. 2D). In SPC-GM mice, MCP-1 levels increased to slightly less than twice the baseline levels, 6 days after infection.

In WT mice, MCP-1 levels rose markedly from very low levels to 32 ng/ml at day 6. TNF-α levels did not change greatly in SPC-GM or WT mice during the first 3 days after infection, and fell in SPC-GM mice to WT levels at day 6.

Interleukin (IL)-10 levels were much higher in SPC-GM than WT mice at day 6 post-infection, suggesting an enhanced anti-inflammatory response in SPC-GM mice. IFN-α is an important component of the innate response to influenza virus (28, 29) and IFN-γ is a major product of CD4+ cells that mediate resistance to influenza (8). Levels of these cytokines were similar in SPC-GM and WT mice (results not shown).

In summary, elevated baseline MCP-1 and TNF-α levels in lungs of SPC-GM mice, combined with the histologic findings and viral burden measurements, indicated that SPC-GM mice mount an early innate immune response that contributes to control of viral infection and reduces lung injury and mortality.

Figure 3:
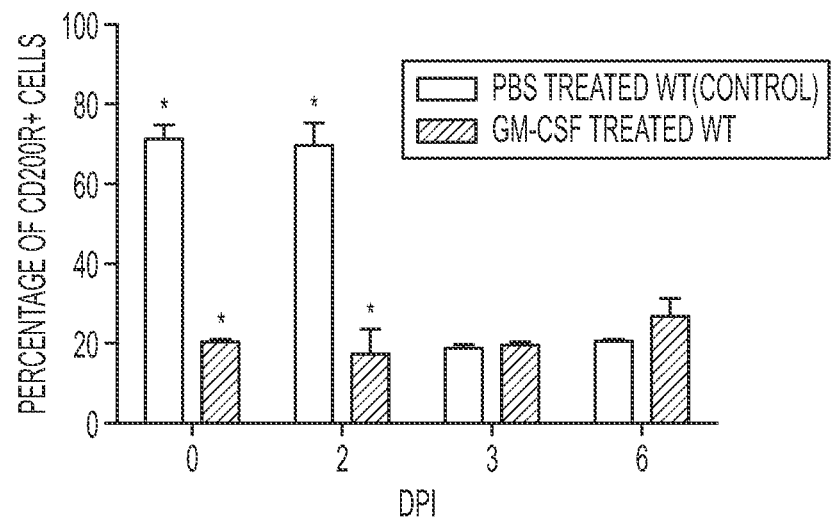
FIG. 3. Expression of CD200R in BAL Cells. WT mice were treated with 1.34 mg/kg of recombinant murine GM-CSF or with PBS for 7 days, prior to infection with PR8 H1N1 influenza. Mice were killed (n=3/time point), and BAL cells were stained with anti-CD200R. Mean values and SEs for the percentages of CD200R+ cells are shown. * p<0.001.
Figure 8A:
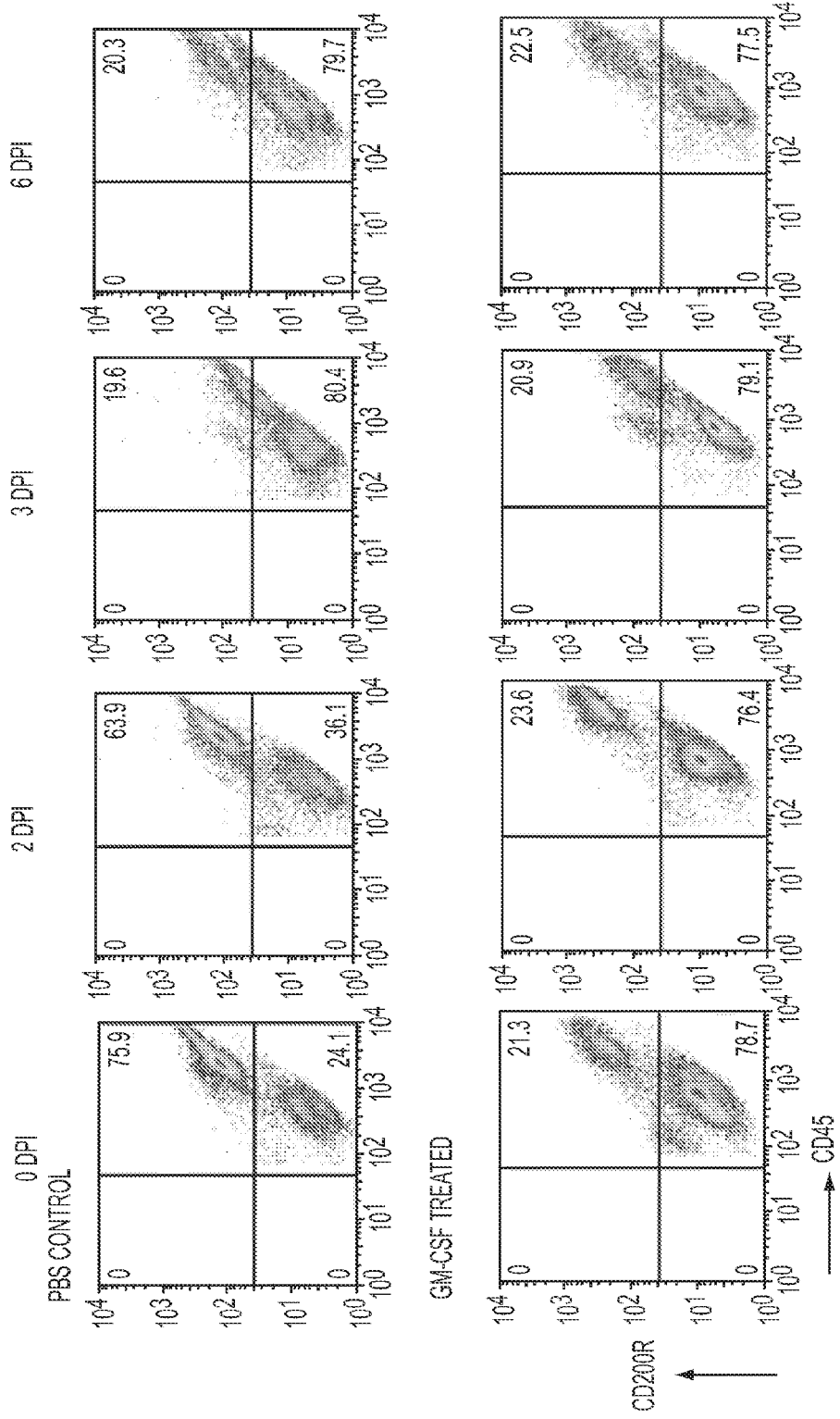
FIG. 8A-8C/E1. Expression of CD200R (FIG. 8A), Gr-1 (FIG. 8B), and CCR2 (FIG. 8C) in BAL cells. WT mice were treated with recombinant murine GM-CSF or with PBS for 7 days, prior to infection with PR8 H1N1 influenza. Three mice were killed at each time point shown, BAL cells were obtained, and stained with antibodies to CD200R, Gr-1 and CCR2. The percentages of positively stained cells were measured by flow cytometry.
Figure 8B:
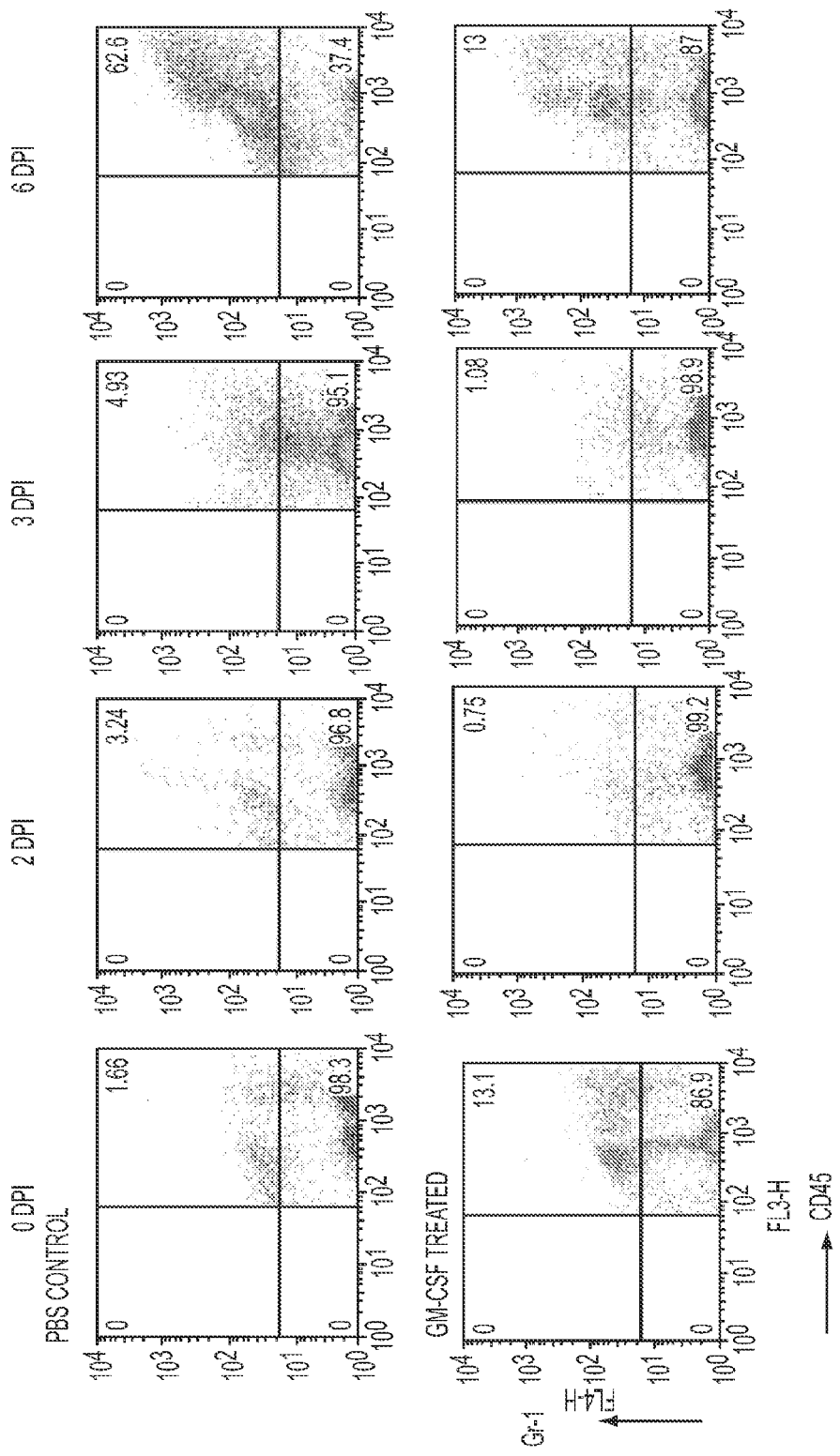
Figure 8C:
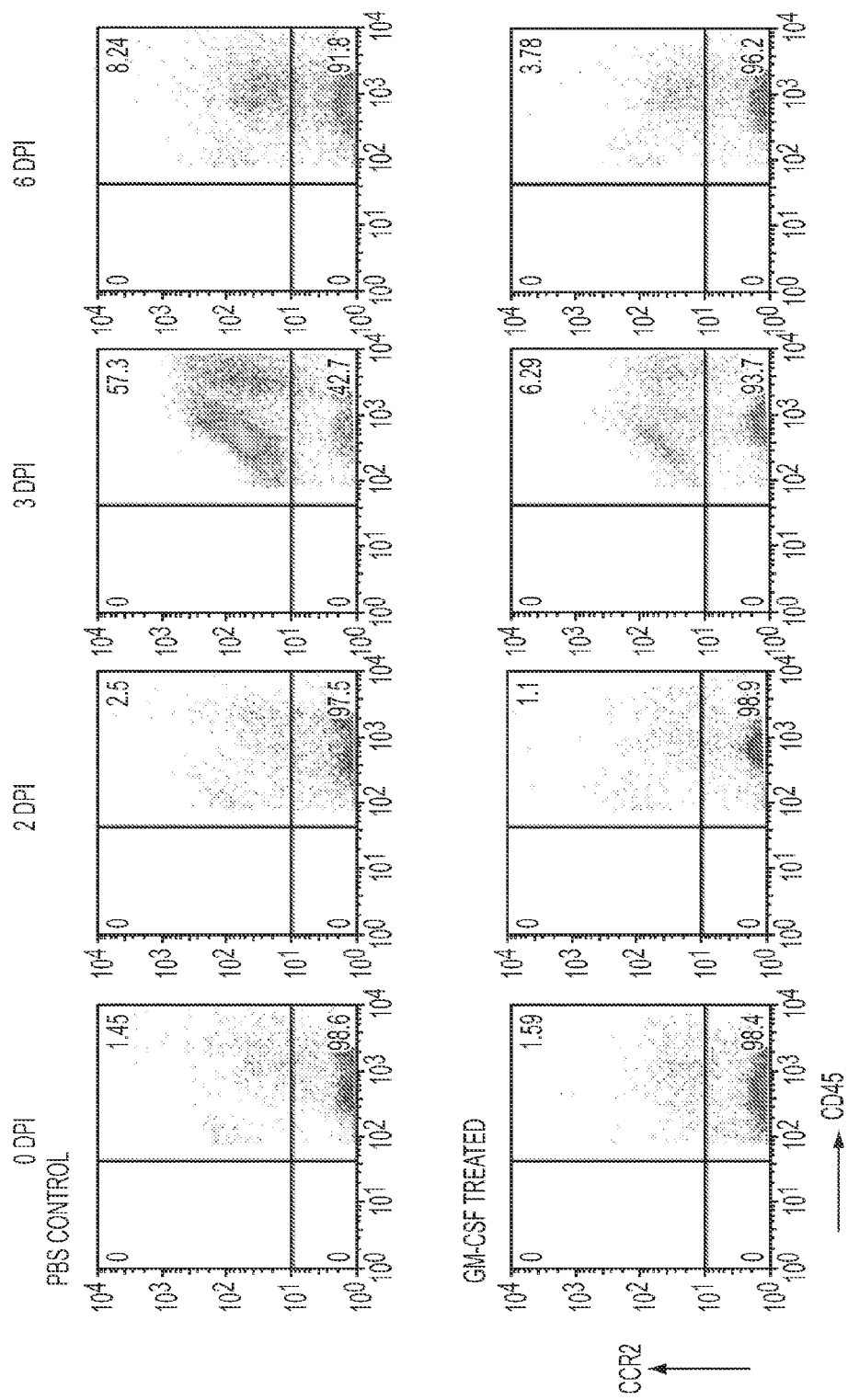

As an alternative means to determine the effect of GM-CSF on the pulmonary inflammatory response during influenza infection, the effect of treating WT mice with GM-CSF was evaluated, using flow cytometry to measure cellular surface markers of inflammation. CD200R and CD200 are an anti-inflammatory receptor-ligand pair that are normally expressed at high levels on AM and on lung epithelial cells, respectively, but are downregulated during inflammation (30, 31). Baseline CD200R levels were greatly reduced in GM-CSF-treated WT mice and increased slightly during infection, whereas levels were much higher in untreated mice at baseline and during the first two days after infection, decreasing at 3 to 6 days after infection (FIG. 3 and FIG. 8A). The percentage of neutrophils, measured by expression of Gr-1, showed higher baseline values in GM-CSF-treated mice but decreased 2-3 days post infection, whereas PBS-treated mice had increased values after infection (FIG. 8B), corresponding to the histologic findings of reduced neutrophil tissue infiltration in SPC-GM mice (FIG. 2C). Expression of CCR2, the major receptor for MCP-1, increased to much higher levels during influenza infection in PBS-treated than in GM-CSF-treated WT mice (FIG. 8C). MCP-1 levels in BAL fluid were also 3-fold higher in untreated than in GM-CSF-treated WT mice 6 days after infection (results not shown), corresponding to the higher lung homogenate MCP-1 levels in WT than in SPC-GM mice (FIG. 2D).

EXAMPLE V

Resistance of SPC-GM Mice to Influenza Depends on Radiation-sensitive Cells That are Not Neutrophils or Lymphocytes SPC-GM mice have increased lung volumes and high numbers of alveolar type II epithelial cells and macrophages (24). To determine if the resistance to influenza in SPC-GM mice was mediated by radiation-resistant structural lung features or by radiation-sensitive myeloid cells, 10 SPC-GM mice were exposed to 50% of a lethal dose of whole-body irradiation (450 rads), and then infected 5 mice with 10 $LD_{50}$ of influenza A virus PR8. All irradiated infected mice died (results not shown), indicating that resistance depends on myeloid cells. Death was not due to irradiation, as the 5 uninfected mice remained well.

Figure 4A:
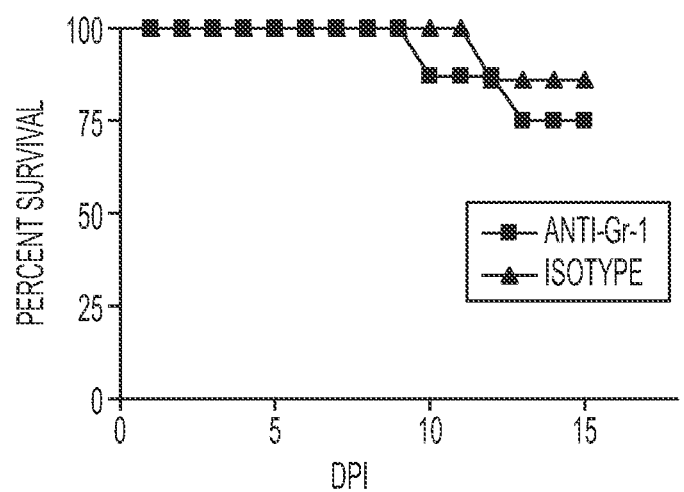
FIG. 4. Resistance to Influenza of SPC-GM Mice does not Require Neutrophils, T Cells or B Cells. (A) SPC-GM mice were treated intraperitoneally with anti-GR1 or isotype control IgG (n=7/group) at days −1, 0, 3 and 6 after infection with 5 $LD_{50}$ of influenza virus PR8, and followed until death or recovery. Anti-GR1 reduced the percentages of neutrophils from 15% to 1% in blood. A representative result of 2 experiments is shown. (B) CD4+ and/or CD8+ T cells were depleted with monoclonal antibodies (n=5-7/group), at −3, 0 and 3 days post-infection with 5 $LD_{50}$ of PR8, and followed until death or recovery. Monoclonal antibodies reduced the percentages of CD4+ and CD8+ cells in the mediastinal lymph nodes from 45% to 0.2%, and from 24% to 2%, respectively. Survival rates did not differ significantly in all groups. (C) SPC-GM mice were treated intraperitoneally with anti-CD90.2 or isotype control IgG (n=7/group) at days −1, 0, 3 and 6 after infection. Mice were infected with 5 $LD_{50}$ of influenza virus PR8 on day 0 and followed until death or recovery. (D) SPC-GM mice were treated with N-acetyl-γ-calicheamicin dimethylhydrazide, conjugated either to anti-CD22 or isotype control antibody (n=5/group) at days −5 and 0 post-infection with 5 $LD_{50}$ of PR8, and followed until death or recovery.
Figure 4B:
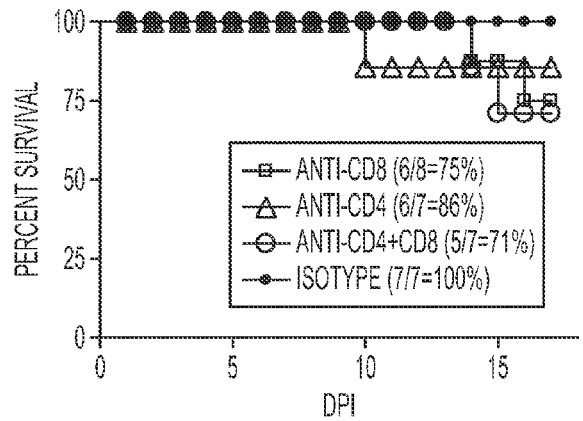
Figure 4C:
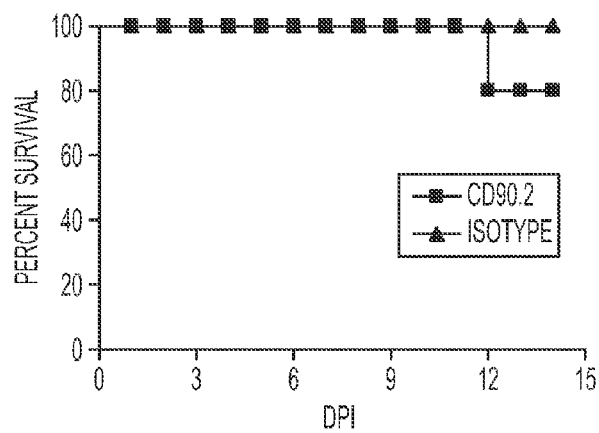
Figure 4D:
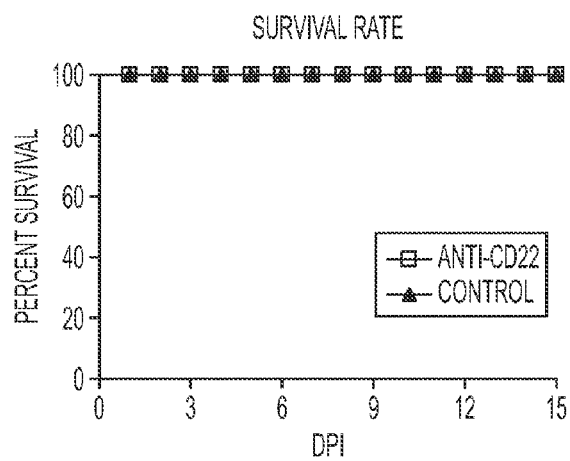

GM-CSF enhances development and maturation of neutrophils and macrophages. The latter can act as innate effectors or become dendritic cells that present antigens to T cells. To identify the cell populations that confer resistance to influenza in SPC-GM mice, different cell types were depleted. Removal of neutrophils from SPC-GM mice with anti-GR1 did not alter resistance to influenza (FIG. 4A). Depletion of CD4+ or CD8+ T cells reduced the survival rate of SPC-GM mice to 80-90%, and depletion of both T cell subsets lowered survival to 70% (FIG. 4B). Depletion of all T cells with anti-CD90.2, which removed CD4+CD8+ cells and γδ T cells, reduced survival to 80% (FIG. 4C). Depletion of B cells with anti-CD22/cal did not reduce survival after influenza infection (FIG. 4D). Therefore, neutrophils, T cells and B cells do not mediate the enhanced resistance of SPC-GM mice to influenza.

EXAMPLE VI

Resistance to Influenza of SPC-GM Mice Requires Alveolar Phagocytes

Figure 5A:
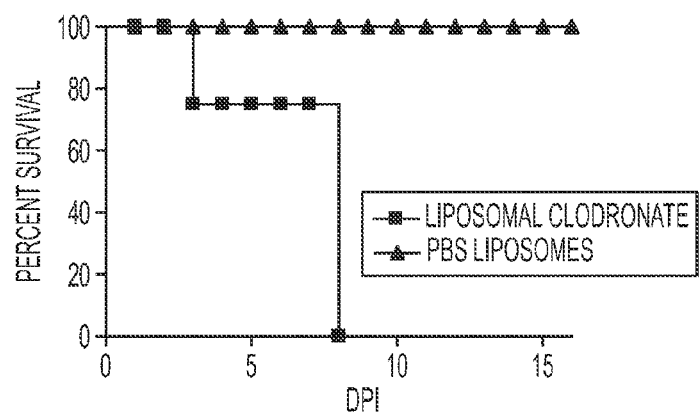
FIG. 5. AM are Required for Resistance of SPC-GM Mice to Influenza. (A) SPC-GM mice were given clodronate-liposomes or PBS-liposomes (n=5/group). Eighteen-24 hours later, mice were infected with 5 $LD_{50}$ of influenza virus PR8, and followed until death or recovery. (B) (B) SPC-GM mice were given clodronate-liposomes or PBS-liposomes 1-6 days after infection with 5 $LD_{50}$ of PR8 (n=3-5/group), and followed until death or recovery. (C) SPC-GM mice were treated with clodronate-liposome to deplete alveolar phagocytes. Three days later, BAL cells (99% AM) from naïve SPC-GM mice were collected. Clodronate-treated SPC-GM mice each received $2\times10^6$ of these AM or PBS intratracheally, and were infected with PR8 16 hours later. A representative of 2 experiments with identical results is shown. (D) WT mice (n=5/group) received $2\times10^6$ BAL cells (99% AM) from naïve SPC-GM mice or PBS intratracheally, and were infected with PR8 16 hours later. A representative result of 2 experiments is shown.
Figure 9:
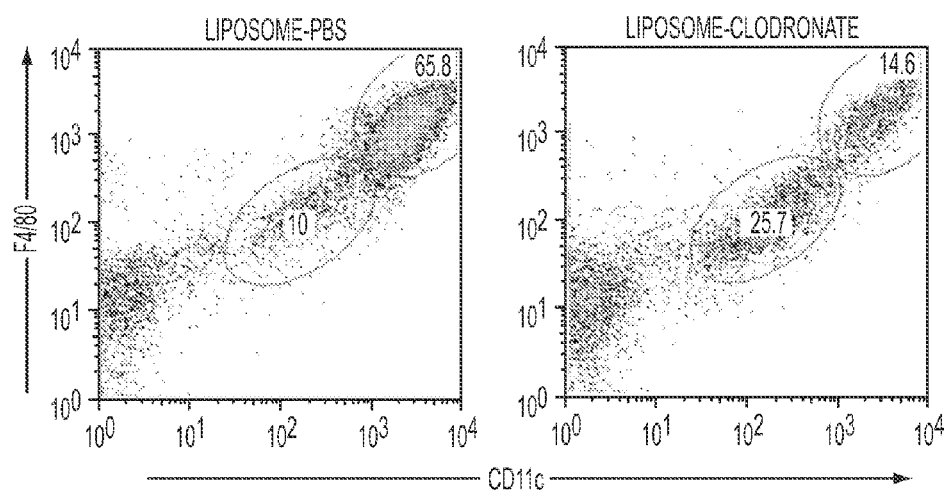
FIG. 9/E2. SPC-GM mice were treated with clodronate-liposome or PBS-liposome and 18 hours later, BAL fluid was collected, stained with antibodies to CD11c, F4/80 and major histocompatibility complex (MHC) class II, and subjected to flow cytometry. Results are shown after gating on MHC class $II^{low}$ AM. A representative of two independent experiments with identical results is shown.

To determine if AM mediate resistance to influenza in SPC-GM mice, intranasal clodronate-liposomes or phosphate buffered saline (PBS)-liposomes were administered before influenza infection. Clodronate is taken up by phagocytes, causing apoptosis and death (32). Clodronate-treated mice all died after influenza infection, but all PBS-liposome-treated mice survived (FIG. 5A). Clodronate depleted 65-84% of the AM from SPC-GM mice (FIG. 9), but did not affect the distribution of macrophages or dendritic cells in lung digests (results not shown), demonstrating that AM are essential for the resistance of SPC-GM mice to lethal influenza.

Figure 5B:
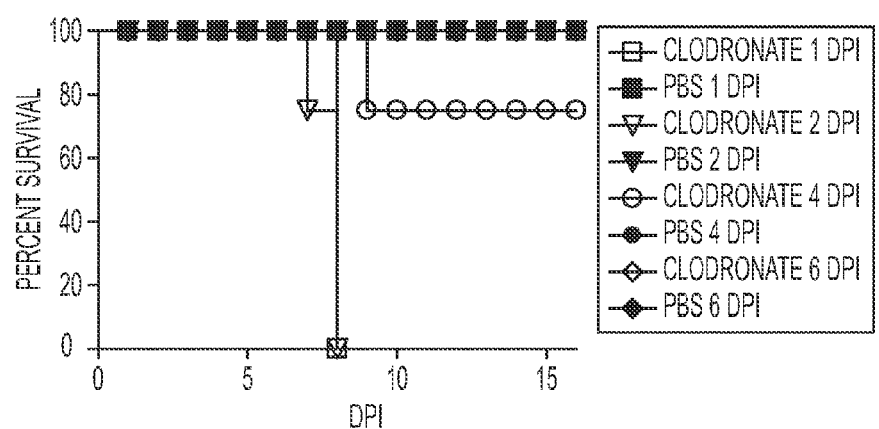

To determine when AM were needed to protect against influenza in SPC-GM mice, clodronate was given 1-6 days after infection. Treatment with clodronate 1-2 days post-infection resulted in 100% mortality, but treatment after 4 days resulted only in 20% mortality, and all SPC-GM mice treated after 6 days survived (FIG. 5B). Therefore, AM were most critical in the first 3 days after infection.

Figure 5C:
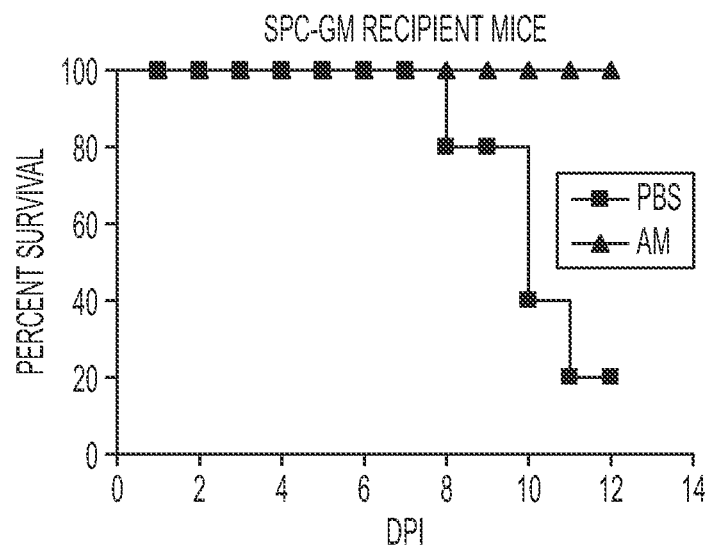
Figure 5D:
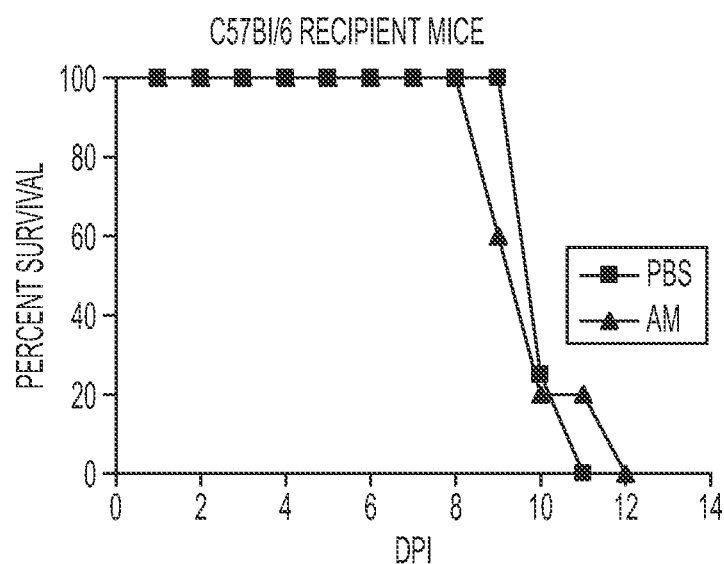

As an alternative means to demonstrate the essential role of AM in resistance to influenza in SPC-GM mice, SPC-GM mice were first treated with clodronate to deplete alveolar phagocytes. Clodronate-treated SPC-GM and WT mice served as recipients. Three days later, recipient mice received PBS intratracheally or AM from naïve SPC-GM donor mice, and were challenged with a lethal dose of PR8 virus 16 hours later. All clodronate-treated SPC-GM mice that received naïve AM survived, whereas 80% of PBS-treated mice died (FIG. 5C). In contrast, AM did not prevent death in WT mice (FIG. 5D).

EXAMPLE VII

AM from SPC-GM Mice Show Reduced Apoptosis After Influenza Infection

Figure 6A:
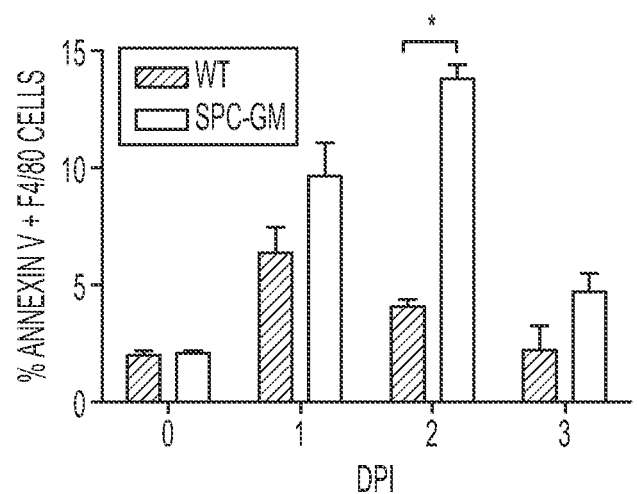
FIG. 6. AM of SPC-GM Mice are More Resistant to Apoptosis than Those of WT Mice. SPC-GM and WT mice were infected with 5 $LD_{50}$ of influenza virus PR8. Bronchoalveolar lavage cells were collected at 0-3 days post infection (DPI) and stained with anti-F4/80 and annexin V or anti-Fas. (A) Mean values and SEs for the percentages of Annexin V+ cells (n=5-6 per time point) are shown. * p<0.05, comparing SPC-GM and WT mice (B). The inventor gated on F4/80+ cells and measured the mean fluorescence intensity (MFI) of Fas. Mean values and SEs for the net MFI of Fas (n=5-6 per time point) are shown. * p<0.05, ** p<0.01, comparing SPC-GM and WT mice. (C) In vitro analysis of apoptosis. AM from naïve SPC-GM and WT mice (n=4/group) were incubated with influenza virus PR8, as detailed in the methods. Cells were stained with anti-F4/80, followed by FITC-Annexin V, and analyzed by flow cytometry. A representative result of 2 experiments is shown.
Figure 6B:
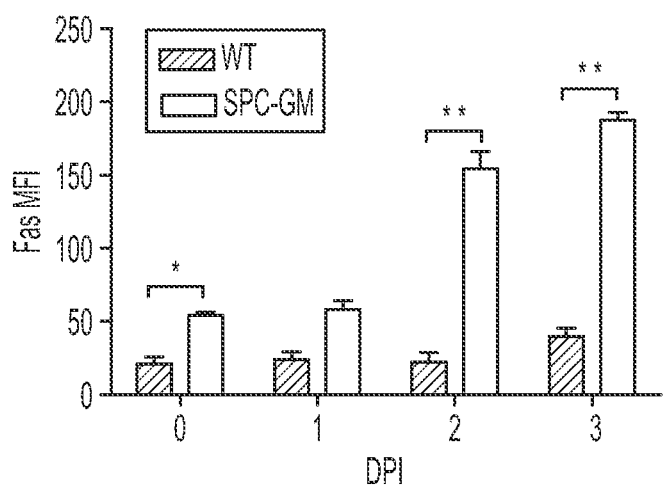
Figure 6C:
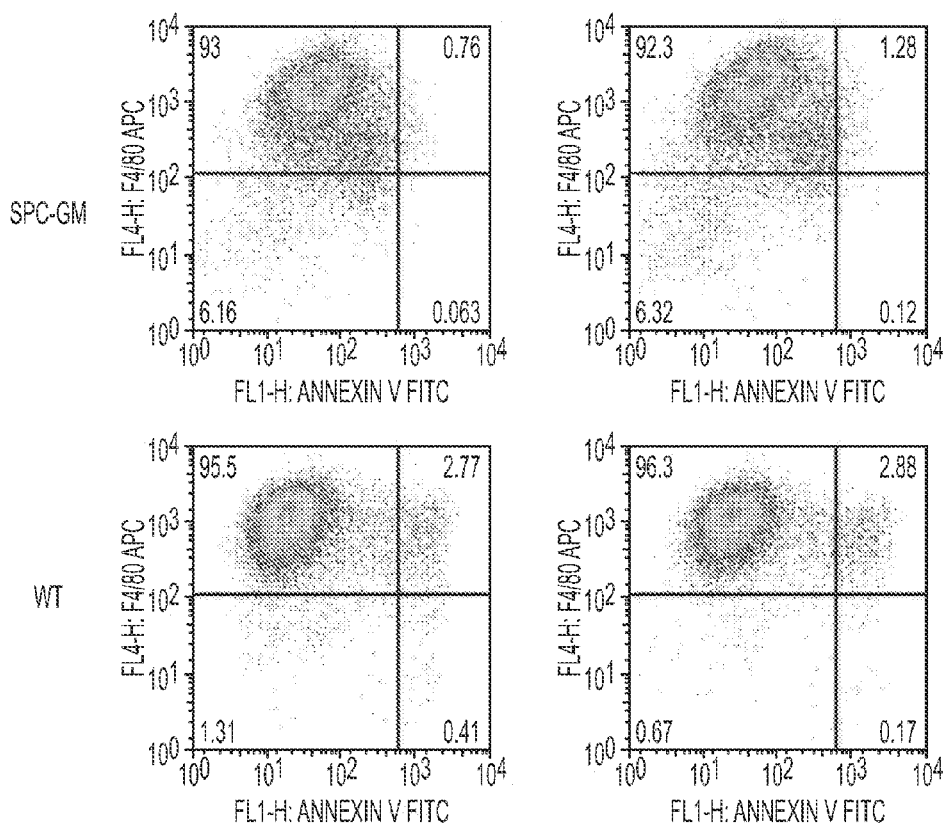
Figure 10A:
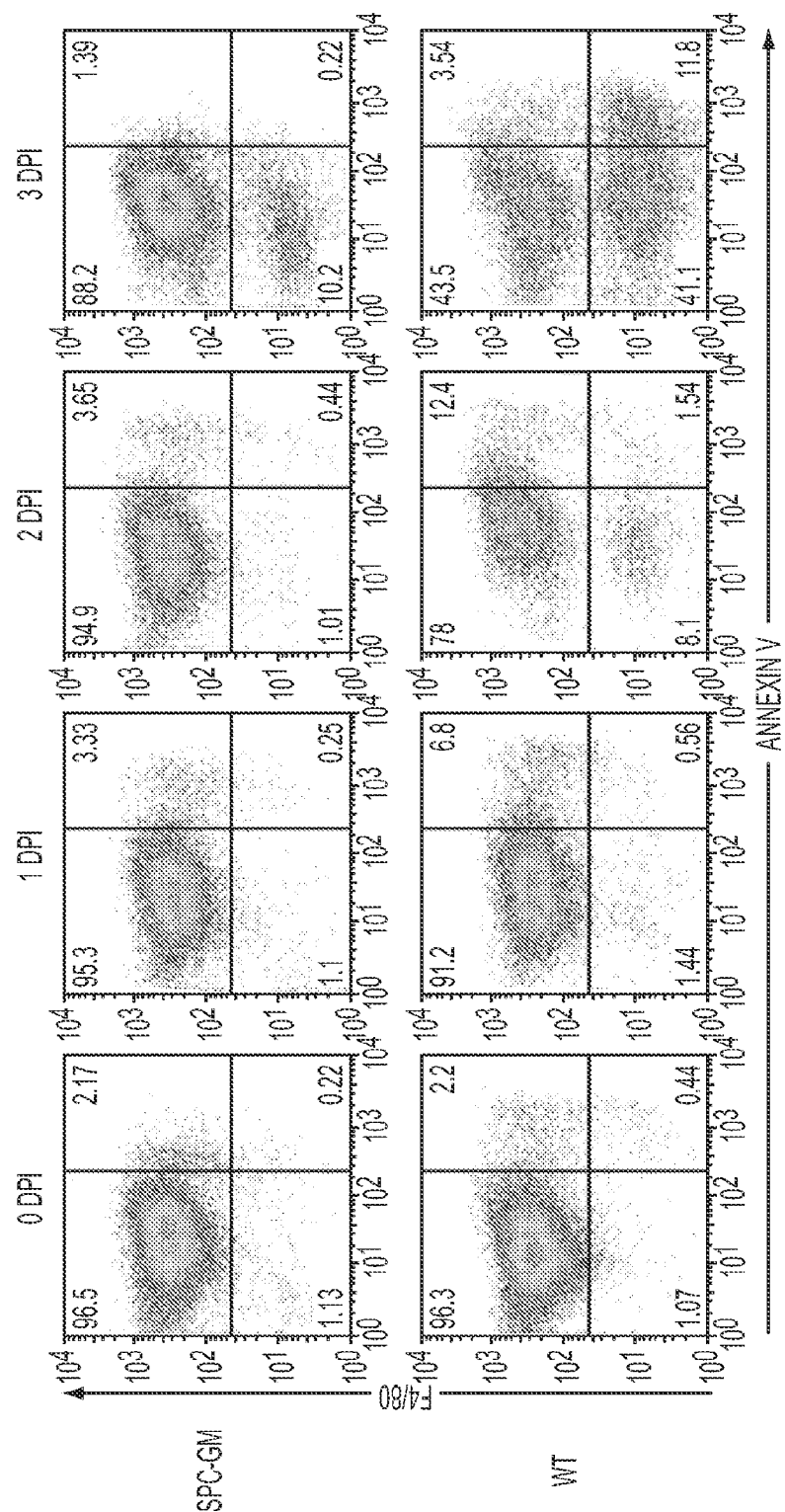
FIG. 10A-10B/E3. AM of SPC-GM Mice are More Resistant to Apoptosis than those of WT Mice. SPC-GM and WT mice were infected with 5 $LD_{50}$ of influenza virus PR8. BAL cells were collected at 0-3 days post infection (DPI) and stained with anti-F4/80 and annexin V or anti-Fas for flow cytometry analysis.
Figure 10B:
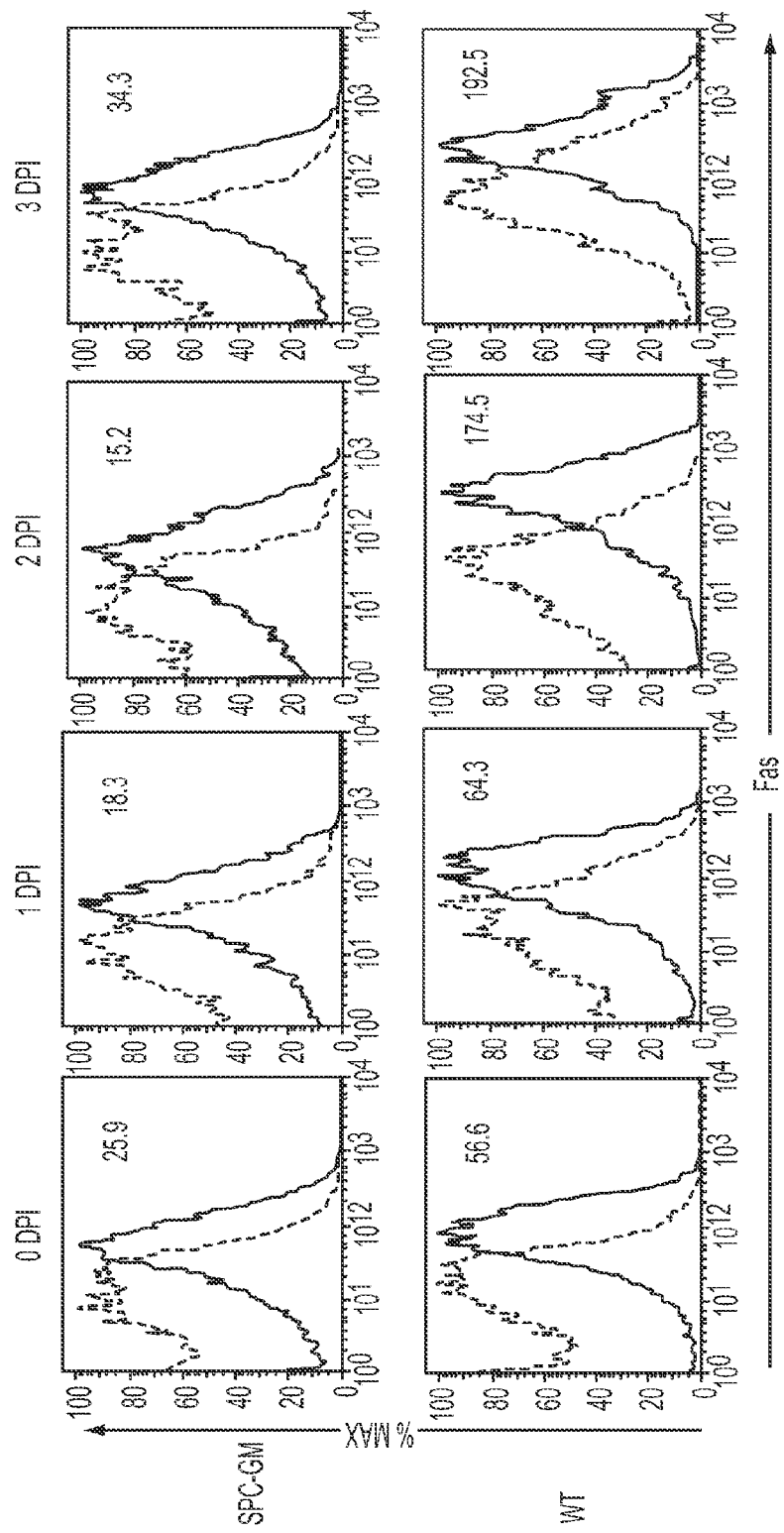

AM are critical to clear infected cells and prevent tissue inflammation. Macrophage apoptosis during influenza infection causes increased mortality and tissue destruction (33). Using immunolabeling and flow cytometry, the percentage of Annexin V+ apoptotic F4/80+AM was found to be 3.5-fold higher in WT than in SPC-GM mice 2 days after influenza infection (FIG. 6A and FIG. 10A). Expression of Fas on AM was 4-7-fold higher in WT than in SPC-GM mice after influenza infection (FIGS. 6B and 10B). The reduced apoptosis in SPC-GM mice could be due in part to the reduced viral burden. To control for this factor, AM from SPC-GM and WT mice were infected with equal numbers of influenza PR8 virus in vitro. The percentage of Annexin V+, apoptotic cells was 2.2-fold higher in AM from WT mice (FIG. 6C).

EXAMPLE VIII

AM from SPC-GM Mice Do Not Have Increased Phagocytic Capacity

Figure 7A:
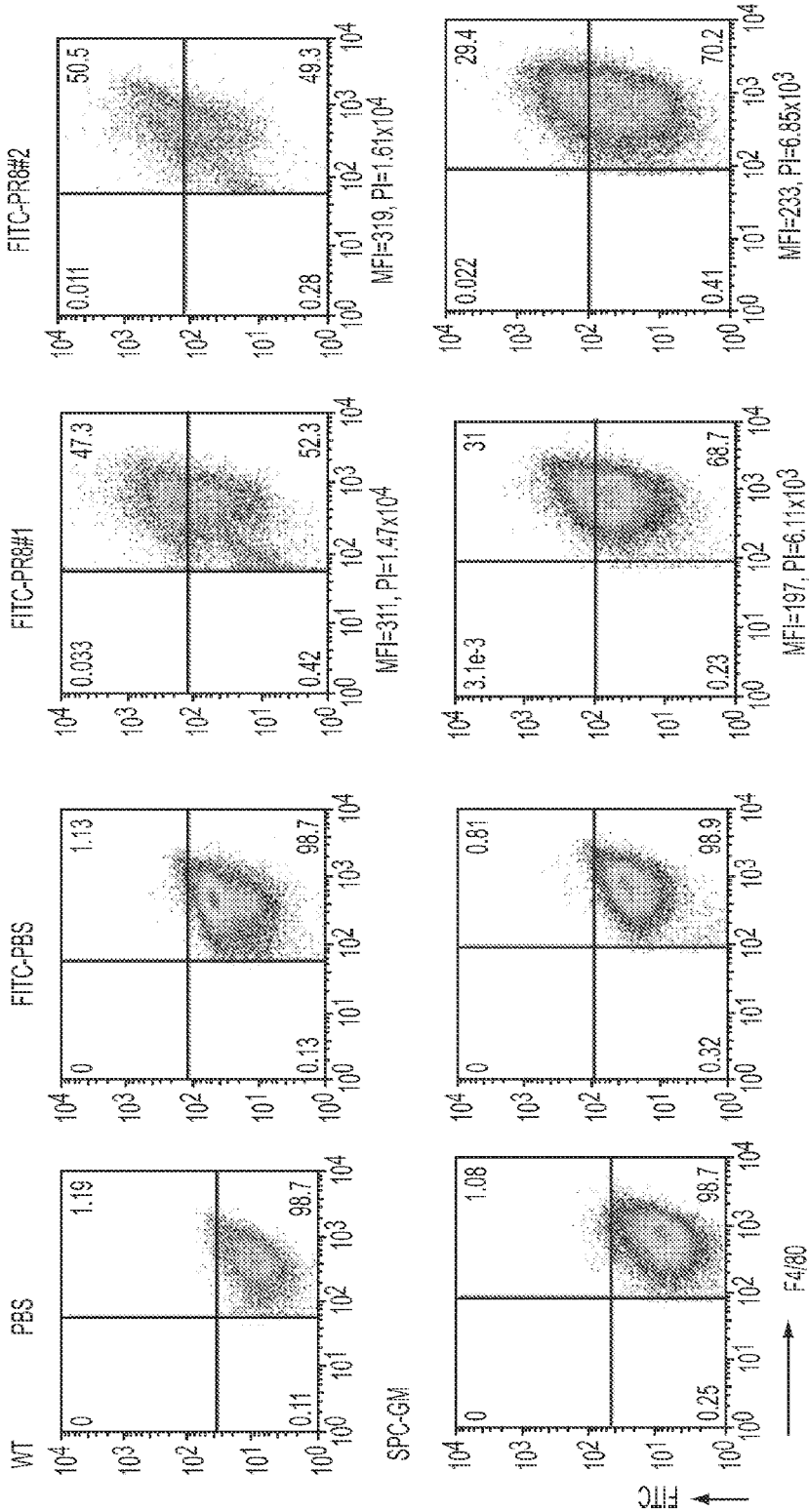
FIG. 7. Phagocytic Capacity of AM from SPC-GM and WT Mice. (A) Mice were intranasally inoculated with FITC-labeled PR8 (n=2), FITC stock in PBS (n=1), or PBS alone (n=1). Two hours later, AM from BAL were stained with allophycocyanin anti-F4/80, and subjected to flow cytometry. The mean fluorescence intensity (MFI) of FITC-labeled PR8 in F4/80+ cells are shown, as is the phagocytic index (PI), which is the percentage of FITC+ F4/80 cells multiplied by the MFI of FITC-labeled PR8 in F4/80+ cells. (B) AM from SPC-GM and WT mice (n=3/group) were cultured with yellow-green FluoSphere Carboxylate-Modified beads. Thirty minutes later, AMs were stained with anti-F4/80 and analyzed by flow cytometry. MFI and PI were calculated, as in panel A.
Figure 7B:
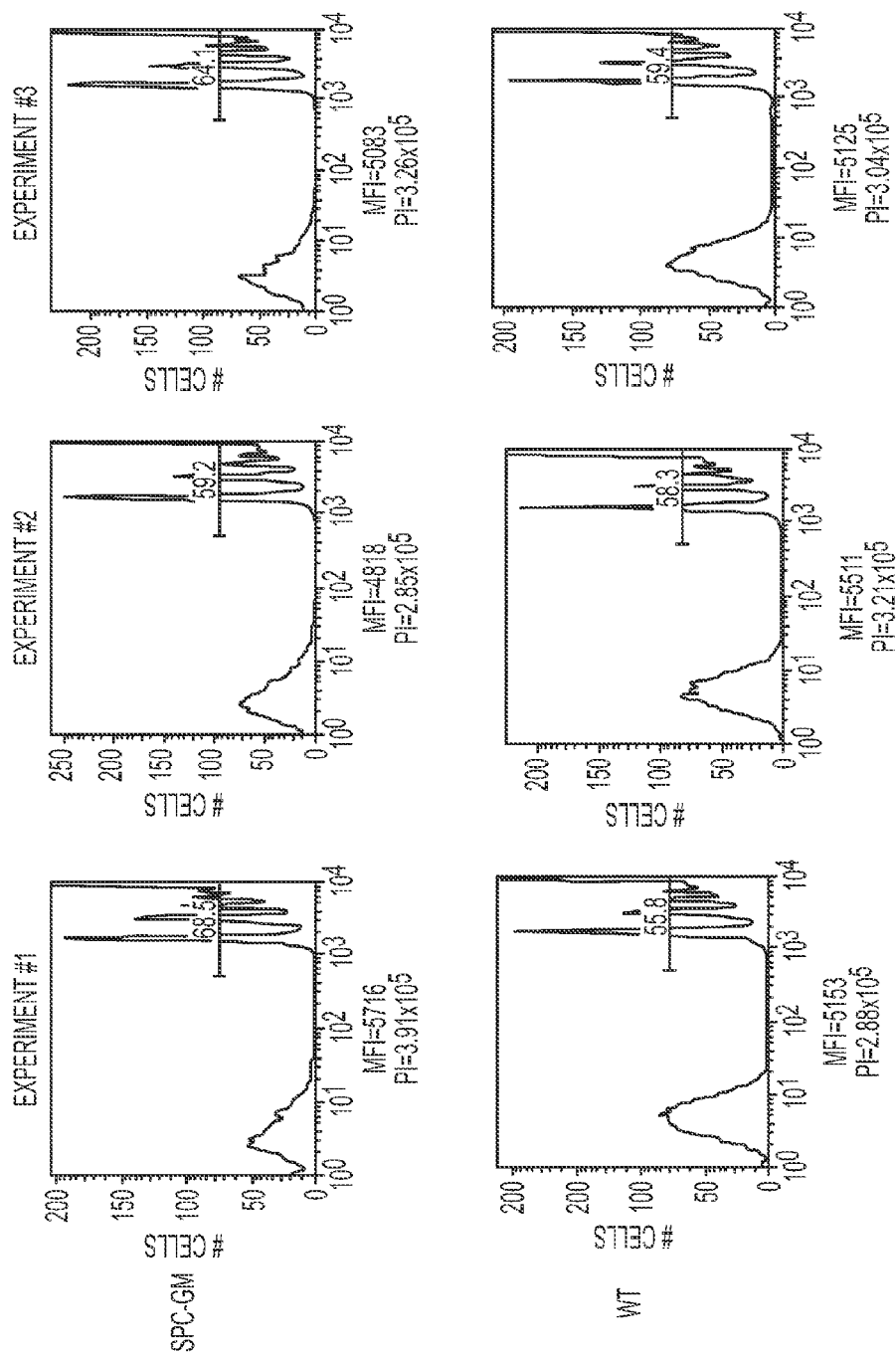

To assess whether resistance of SPC-GM mice to influenza was due to increased virus uptake by AM in vivo, FITC-labeled PR8 virus was administered intranasally to SPC-GM and WT mice, and the percentages of AM that contained virus were measured, as were the phagocytic index (percentage of virus-containing AM x mean fluorescence intensity). AM from SPC-GM and WT mice had similar phagocytic activity (FIG. 7A). When AM were exposed to fluorophore-labeled beads in vitro, the phagocytic activity of AM from SPC-GM and WT mice were also similar (FIG. 7B).

EXAMPLE IX

Use of Pulmonary GM-CSF to Prevent and Treat Acute Pulmonary Infections

Lung is the portal of entry for many virulent pathogens, such as avian influenza H5N1 and select agents such as *B. anthracis, Francisella tularensis* and *Y. pestis*, which are often lethal despite therapy. Even seasonal influenza annually infects 5-20% of the U.S. population, causing >200,000 hospitalizations and 40,000 deaths and the recent H1N1 pandemic has inflicted significant morbidity and mortality.

For decades, using vaccines to stimulate adaptive immunity has been the main tool to prevent pulmonary infections due to viruses and bacteria, including influenza, *Streptococcus pneumoniae* and *Bordetella pertussis*. This conventional approach is convenient and targets specific pathogens but requires known biological preparations such as vaccine strains of pathogens, immunogenic antigens or epitopes to induce or improve immunity to a particular disease. Also, in almost all cases, 2-4 weeks and sometimes more than one inoculation is required for protection.

Pneumonia due to H5N1 influenza causes extensive pulmonary edema and lung injury, with massive infiltration of cells into the alveoli and alveolar hemorrhage. Although infiltration of immune cells into the inflamed lung is required for host protection and recovery, excessive and dysregulated immune responses can exacerbate clinical symptoms and contribute to potentially lethal lung damage and pathology. An overexuberant immune responses can damage epithelial cells and impair respiratory gas exchange, causing severe reactions to viral antigens that lead to hospitalization and/or death. It has also been shown that influenza virus replicates undetected for at least 48 hrs, thus preventing the immediate initiation of innate and adaptive immunity.

According to the present invention, as described and exemplified above, the present inventor was the first to demonstrate that that delivery of GM-CSF to the lungs stimulates innate immunity in the lungs and induces robust protection against lethal influenza virus infections by enhancing alveolar phagocyte function. By delivering GM-CSF to the lung, this strategy reduces the risk of systemic toxicity and maximizes efficacy of therapy at the disease site.

GM-CSF can also protect against secondary bacterial pneumonia and enhance innate immunity against multiple pathogens. Pulmonary delivery of GM-CSF is an unconventional approach that is based on stimulating host innate immunity that is not pathogen or antigen dependant. Hence, in the case of pandemics of pulmonary acute infections or pulmonary infections with select agents that are almost 100% lethal, it is deployed to increase the pulmonary innate immunity and consequently protect mass populations against lethal pulmonary infections from unknown origin in a short period of time.

The present invention also provides for using aerosolized recombinant GM-CSF as a therapeutic agent to treat acute infectious pneumonia that is caused not only by influenza infections, including by avian influenza H5N1, but also by agents such as *Bacillus anthracis, Francisella tularensis* and *Yersinia pestis*. For this route of administration, high doses of GM-CSF (~100-500-times higher than a systemic dose) is used in the lungs to activate AMs.

Figure 11A:
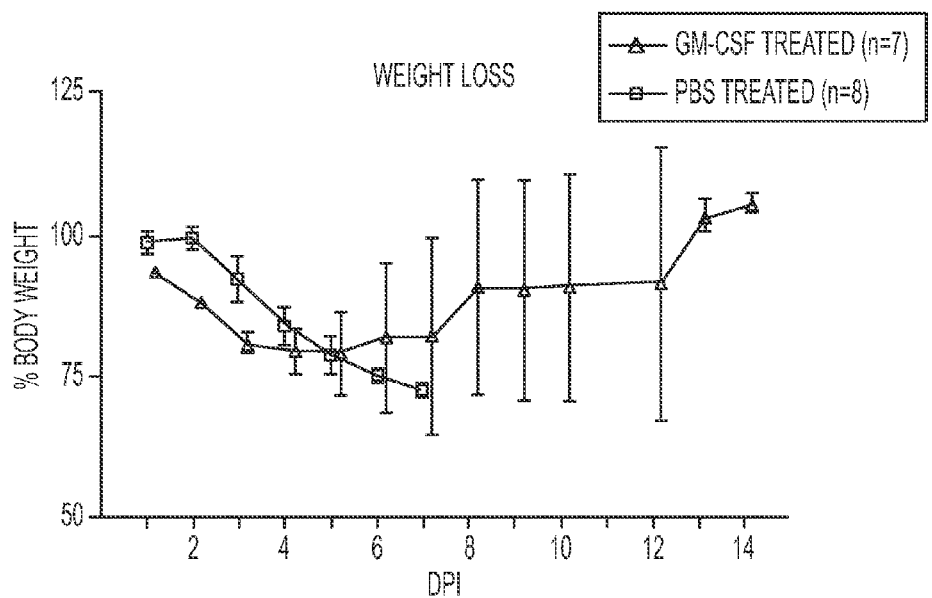
FIG. 11A-B. Treating Wild Type Mice with GM-CSF After Infection with Influenza A Virus. C57Bl/6 wild type mice were infected with a lethal dose of PR8 virus and treated with ~1 μg/g body weight of rGM-CSF (or PBS) at 6 hrs, 1 and 2 day post infection. Mice were monitored for weight loss (FIG. 11A) and mortality (FIG. 11B).
Figure 11B:
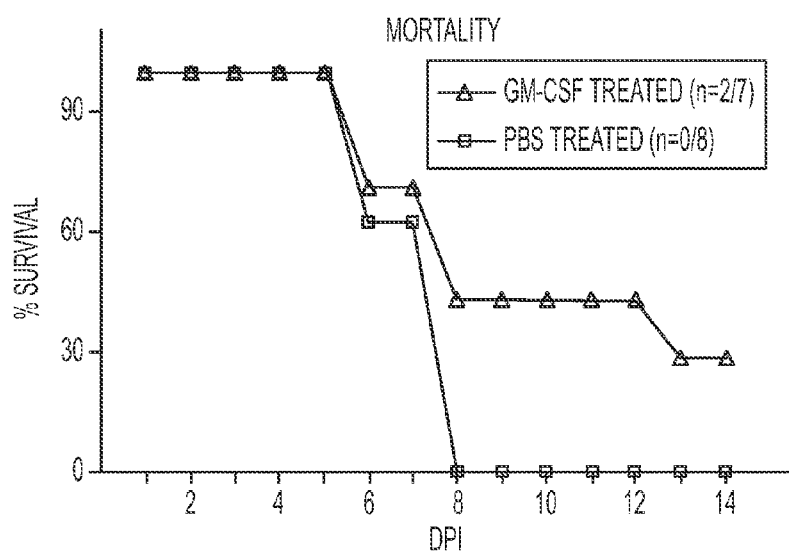

In a model of treating viral pneumonia that occurs subsequent to influenza infection, C57B1/6 wild type mice were infected with a lethal dose influenza A virus PR8 and treated with ~1 μg/g body weight of rGM-CSF at 6 hrs, 1 and 2 day post infection. Mice were monitored for weight loss and mortality. Results appear in FIGS. 11A and B. Surviving mice regained their pre-infection weight and remained well for at least 2 additional weeks.

EXAMPLE X

Use of GM-CSF Conjugated to PEG and Nanoparticles

Lung injury induced by aforementioned acute infections induce a porous lung vasculature that facilitates the escape of GM-CSF from the alveolar space. Hence, according to the present invention, higher doses of GM-CSF are retained in the alveolar space for activation of AMs, and this is coupled with blocking entry of the GM-CSF into the circulation to prevent systemic toxicity.

These goals are achieved using rGM-CSF conjugated/covalently bonded to, or inserted into, NPs. The preferred size of NPs for this embodiment are those larger than the size of the pores in injured lung vasculature. The endothelial cell lining of the pulmonary vasculature forms a semipermeable barrier between the blood and the lung interstitium and epithelial cell lining of alveoli forms a barrier between alveolar space and the interstitium. Pulmonary infections such as influenza disrupt the barriers' integrity and result in movement of fluid and macromolecules into and from alveoli. GM-CSF is conjugated to NPs of a size that do not pass through the lung vasculature which also promotes retention in the alveolar space of the therapeutic agent that has been delivered to injured lungs.

Figure 12:
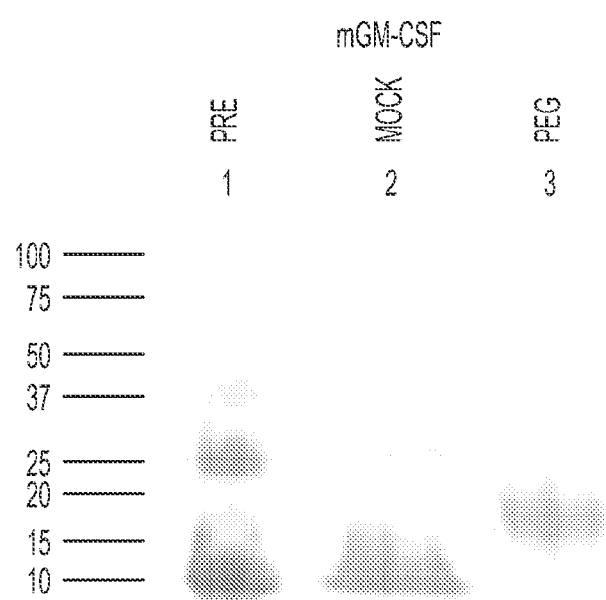
FIG. 12: SDS-Polyacrylamide Gel Electrophoresis of Murine GM-CSF After PEGylation. 4 μg of recombinant mouse GM-CSF starting material (lane 1), mock-treated material (lane 2) and PEGylated material (lane 3) were electrophoresed through a sodium dodecyl sulfate (SDS) 8-25% polyacrylamide gel (Phastgel) and stained with Coomassie Blue. Samples were reduced with dithiothreitol (DTT) and boiled in loading dye before loading. The original starting material contains a higher molecular weight band that is a dimer of GM-CSF. The PEGylated material is approximately 18 kD, compared to 11 kD for the mock-treated material, indicating the addition of PEG.

As described above, NP's of diameters greater than 10 nm are used for this purpose. Initial studies were performed by PEGylation of rGM-CSF. Standard amine-coupling chemistry was used with a PEG 12mer with methyl and amine-reactive NHS-ester groups at opposite ends $(MS(PEG)_{12})$. Since the NHS moiety spontaneously reacts with primary amines, GM-CSF was prepared in bicarbonate buffer, pH 8.2, mixed with an appropriate amount of reagent and allowed to react at room temperature for several hours. The reaction is stopped by rapid desalting over a mini desalting column and the resulting PEG-protein dialyzed into PBS buffer. The PEG-GM-CSF will be analyzed by SDS-PAGE to confirm addition of random PEG chains, with corresponding increases in molecular weight. GM-CSF contains 11 lysine residues and the N-terminus, any or all of which may be PEGylated. Results of an initial study are shown in FIG. 12. In this study 4 μg of recombinant mouse GM-CSF starting material (lane 1), mock-treated material (lane 2) and PEGylated material (lane 3) were electrophoresed through an SDS 8-25% polyacrylamide gel (Phastgel) and stained with Coomassie Blue. Samples were reduced with DTT and boiled in loading dye before loading. The original starting material contains a higher molecular weight band that is a dimer of GM-CSF. The PEGylated material is approximately 18 kD, compared to 11 kD for the mock-treated material, indicating the addition of PEG.

Discussion of Examples I-X

Most studies of the immune response to influenza have focused on the importance of antibody production by B cells and cytolytic activity of CD8+ T cells in mediating protection against infection. The present invention provides a novel means of conferring marked resistance to influenza through enhancing innate immune mechanisms that depend on AM. SP-C GM mice that overexpress GM-CSF only in the lungs were discovered to be highly resistant to infection with laboratory and clinical influenza strains, including the pandemic swine H1N1 strain. SPC-GM mice had no mortality, and markedly reduced lung injury and alveolar damage after influenza infection (FIGS. 1, 2). Resistance to influenza was unaffected by depletion of neutrophils, T cells and B cells, but was completely abrogated by elimination of alveolar phagocytes and reconstituted by intratracheal transfer of naïve AM (FIGS. 4, 5).

AM from SPC-GM mice were more resistant to influenza-induced apoptosis (FIG. 6). These mice showed increased baseline lung levels of MCP-1 and TNF-α and earlier histologic evidence of mononuclear cell infiltrates after influenza infection, indicating development of a more rapid host inflammatory response that reduced viral burden (FIG. 2). Similarly, delivery of GM-CSF to the lungs of WT mice increased lung MCP-1 and TNF-α levels, reduced viral burden and conferred resistance to influenza (FIG. 1C), emphasizing the therapeutic usefulness of these findings.

Current strategies to combat influenza focus on vaccines and antiviral agents. Vaccines are designed to elicit antibody responses against hemagglutinin and neuraminidase antigens in influenza viruses that circulated in the preceding influenza seasons. However, antigenic drift and the emergence of new strains require constant formulation of modified vaccines, the production of which may not be quick enough to protect the population at risk. In addition, stockpiled current vaccines may be ineffective against future outbreaks. The efficacy of antiviral agents has also been reduced by the rapid spread of drug-resistant influenza strains.

The present invention of using GM-CSF provides an alternative strategy to ameliorate disease due to influenza. rhGM-CSF was recently shown to protect against lethal influenza infection in mice (23). The present inventor extended those observations to additional influenza strains, including, importantly, the recent pandemic swine H1N1 strain.

Intravenous and subcutaneous GM-CSF is in current use to treat neutropenia and bone marrow suppression and is well tolerated. Intranasal or aerosol delivery will minimize toxicity while maximizing effects on AM. By stimulating innate immunity that does not require recognition of strain-specific antigens, GM-CSF is expected to be effective against a broad range of influenza strains, and resistance to its effects are unlikely to develop.

MCP-1 and TNF-α can exhibit dichotomous effects during influenza infection. MCP-1 contributes to protection against influenza, based on the observation that MCP-1 gene-deleted mice show greater weight loss and higher viral burdens compared to infected WT mice (34); neutralization of MCP-1 causes increased alveolar epithelial cell damage (35). However, highly pathogenic H5N1 influenza strains elicit greater MCP-1 production by human macrophages than do H1N1 strains (36), and inhibition of MCP-1 production reduces inflammation during influenza infection (37). These observations suggest that uncontrolled MCP-1 production contributes to lung injury. In the case of TNF-α, elevated levels are typical of infection with highly pathogenic H5N1 influenza strains in animal models (37, 38), and inhibition of TNF-α reduces disease severity (39). On the other hand, TNF-α markedly reduces influenza virus replication in lung epithelial cells (40), and induction of pulmonary TNF-α before influenza infection reduces mortality, viral titers and lung inflammation (41), demonstrating that early TNF-α production contributes to protection.

In the above studies, SPC-GM mice had elevated baseline lung MCP-1 and TNF-α levels without histologic evidence of inflammation, and these levels remained relatively stable during influenza infection, associated with a reduced viral burden and resolution of lung inflammation. In contrast, in WT mice, MCP-1 levels rose markedly to >30 ng/ml during infection, associated with severe lung injury and death. When WT mice were treated with intranasal GM-CSF prior to influenza infection, they also developed high baseline MCP-1 and TNF-α levels that changed little during infection, accompanied by reduced viral titers, compared to PBS-treated mice. In combination with published studies cited above, the present findings indicate that MCP-1 and TNF-α contribute to the potent early innate immune response to influenza in SPC-GM mice, which controls infection and prevents uncontrolled cytokine release, thereby limiting tissue injury. SPC-GM mice also produced more IL-10 at later stages of infection (FIG. 2D), which is important in limiting pulmonary inflammation (42).

Adaptive immunity is known to be important for protection against influenza infection in animal models and in humans, with substantial published evidence supporting the role of antibodies and CD8+ T cells in mediating these effects (1-6). However, recent studies indicate that AM are also essential for effective defense against influenza. Depletion of AM increased the viral burden and markedly increased mortality from H1N1 influenza in pigs (13), H3N2 influenza in mice (43) and H1N1 influenza bearing the hemagglutinin and neuraminidase of the 1918 pandemic strain (14). AM are the major source of IFN-α during pulmonary infection with RNA viruses (43) and can phagocytose influenza virus through Fc receptor-mediated phagocytosis (12) and through opsonization with surfactant protein A (44). In addition, AM can phagocytose necrotic and apoptotic epithelial cells generated during infection, preventing release of cellular debris and proteinases that would otherwise stimulate cytokine production, lung injury and reduced vascular integrity (33). Influenza virus induces apoptosis of macrophages (45), and CCL5-CCR5 signaling reduces macrophage apoptosis, enhancing viral clearance and reducing lung inflammation and death (33).

GM-CSF is essential for differentiation of AM, and mice with a deleted GM-CSF gene have defective phagocytosis of adenovirus, reduced bacterial killing, Toll-like receptor-mediated signaling and TNF-α production, and impaired metabolism of surfactant (26, 46-48). GM-CSF also affects lung structure, as SPC-GM mice have enhanced proliferation and hyperplasia of alveolar epithelial cells (24), reduced apoptosis of alveolar epithelial cells and improved alveolar barrier function after exposure to hyperoxia (49). The resistance of SPC-GM mice to influenza was abrogated by administration of clodronate and restored by transfer of AM, indicating that AM are necessary to confer this resistance. The present results show that GM-CSF markedly increases resistance to influenza by increasing the number of AM. SPC-GM mice have 5-10 times more AM than WT mice (24), and this difference was amplified during the critical first three days after influenza infection, when apoptosis was greatly reduced in AM from SPC-GM mice, compared to WT animals. Levels of Fas were increased on AM from WT mice, consistent with previous findings that macrophage apoptosis during influenza infection is mediated through the Fas/FasL extrinsic pathway (50). GM-CSF induces expression of the anti-apoptotic proteins, mcl-1 and bcl-2, in hematopoietic cells (51, 52), and AM from SPC-GM mice are likely to be relatively resistant to apoptosis. Although the phagocytic capacity of individual AM from SPC-GM and WT mice was similar, the greatly increased numbers of AM in SPC-GM mice should enhance uptake of influenza virus and ingestion and clearance of dead and dying epithelial cells, reducing lung injury. Although GM-CSF modulates differentiation of dendritic cells (16), these effects were not central to the capacity of GM-CSF to confer resistance to influenza, as depletion of T cells and B cells did not abrogate influenza resistance.

Three influenza strains were evaluated above. GM-CSF will therefore be effective for other clinical influenza isolates as well as other viruses such as hantavirus.

In the present experimental systems, high GM-CSF levels were present in the lung prior to influenza infection. Because treatment of influenza with GM-CSF in the clinical setting is much more feasible and cost-effective when delivered after development of symptoms, the present invention is directed to treatment after infection as well. The present inventor has found (see Example IX) that delivery of GM-CSF to WT mice after lethal influenza infection reduced mortality from 100% to 70%. Delivering GM-CSF in an inhalation chamber or use of water-in-fluorocarbon emulsions may be better suited for drug delivery to edematous alveoli.

In summary, the present invention provides a novel means to confer marked resistance to influenza by enhancing innate immune mechanisms that depend on AM. GM-CSF in the lung resulted in mice that were highly resistant to influenza virus infection, and was mediated through AM, which showed increased resistance to apoptosis. Delivery of GM-CSF to the lungs after the onset of symptoms will also improve the outcome of influenza infection, making this strategy a new therapeutic approach to reduce morbidity and mortality from influenza in humans.

All references cited above in the body of this document (and in the list below) are incorporated by reference herein in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

REFERENCES CITED

1. Coro E S, Chang W L, and Baumgarth N. Type I IFN receptor signals directly stimulate local B cells early following influenza virus infection. *J Immunol* 2006; 176: 4343-4351.
2. Kuwano K, Scott M, Young J F, and Ennis F A. HA2 subunit of influenza A H1 and H2 subtype viruses induces a protective cross-reactive cytotoxic T lymphocyte response. *J Immunol* 1988; 140:1264-1268.
3. Kuwano K, Braciale T J, and Ennis F A. Cytotoxic T lymphocytes recognize a cross-reactive epitope on the transmembrane region of influenza H1 and H2 hemagglutinins. *Viral Immunol* 1989; 2:163-173.
4. Kuwano K, Tamura M, and Ennis F A. Cross-reactive protection against influenza A virus infections by an NS1-specific CTL clone. *Virology* 1990; 178:174-179.
5. Mackenzie C D, Taylor P M, and Askonas B A. Rapid recovery of lung histology correlates with clearance of influenza virus by specific CD8+ cytotoxic T cells. *Immunology* 1989; 67:375-381.

6. Yamada A, Young J F, and Ennis F A. Influenza virus subtype-specific cytotoxic T lymphocytes lyse target cells coated with a protein produced in *E. coli*. *J Exp Med* 1985; 162:1720-1725.
7. Brown D M, Roman E, and Swain S L. CD4 T cell responses to influenza infection. *Semin Immunol* 2004; 16:171-177.
8. Brown D M, Dilzer A M, Meents D L, and Swain S L. CD4 T cell-mediated protection from lethal influenza: perforin and antibody-mediated mechanisms give a one-two punch. *J Immunol* 2006; 177:2888-2898.
9. Jelley-Gibbs D M. Influencing the fates of CD4 T cells on the path to memory: lessons from influenza. 2008.
10. Swain S L, Agrewala J N, Brown D M, Jelley-Gibbs D M, Golech S, Huston G, Jones S C, Kamperschroer C, Lee W H, McKinstry K K, et al. CD4+ T cell memory: generation and multi-faceted roles for CD4+ T cells in protective immunity to influenza. *Immunol Rev* 2006; 211:8-22.
11. Lau Y F, Tang L H, Ooi E E, and Subbarao K. Activation of the innate immune system provides broad-spectrum protection against influenza A viruses with pandemic potential in mice. *Virology* 2010; 406:80-87.
12. Huber V C, Lynch J M, Bucher D J, Le J, and Metzger D W. Fc receptor-mediated phagocytosis makes a significant contribution to clearance of influenza virus infections. *J Immunol* 2001; 166:7381-7388.
13. Kim H M, Lee Y W, Lee K J, Kim H S, Cho S W, Van Rooijen N, Guan Y, and Seo S H. Alveolar macrophages are indispensable for controlling influenza viruses in lungs of pigs. *J Virol* 2008; 82:4265-4274.
14. Tumpey T M, Garcia-Sastre A, Taubenberger J K, Palese P, Swayne D E, Pantin-Jackwood M J, Schultz-Cherry S, Solorzano A, Van Rooijen N, Katz J M, et al. Pathogenicity of influenza viruses with genes from the 1918 pandemic virus: functional roles of alveolar macrophages and neutrophils in limiting virus replication and mortality in mice. *J Virol* 2005; 79:14933-14944.
15. Shi Y, Liu C H, Roberts A I, Das J, Xu G, Ren G, Zhang Y, Zhang L, Yuan Z R, Tan H S, et al. Granulocyte-macrophage colony-stimulating factor (GM-CSF) and T cell responses: what we do and don't know. *Cell Res* 2006; 16:126-133.
16. Min L, Mohammad Isa S A, Shuai W, Piang C B, Nih F W, Kotaka M, and Ruedl C. Cutting edge: granulocyte-macrophage colony-stimulating factor is the major CD8+ T cell-derived licensing factor for dendritic cell activation. *J Immunol* 2010; 184:4625-4629.
17. Tazawa R, Hamano E, Arai T, Ohta H, Ishimoto O, Uchida K, Watanabe M, Saito J, Takeshita M, Hirabayashi Y, et al. Granulocyte-macrophage colony-stimulating factor and lung immunity in pulmonary alveolar proteinosis. *Am J Respir Crit Care Med* 2005; 171:1142-1149.
18. Paine R, III, Morris S B, Jin H, Wilcoxen S E, Phare S M, Moore B B, Coffey M J, and Toews G B. Impaired functional activity of alveolar macrophages from GM-CSF-deficient mice. *Am J Physiol Lung Cell Mol Physiol* 2001; 281:L1210-L1218.
19. Ballinger M N, Paine R, III, Serezani C H, Aronoff D M, Choi E S, Standiford T J, Toews G B, and Moore B B. Role of granulocyte macrophage colony-stimulating factor during gram-negative lung infection with *Pseudomonas aeruginosa*. *Am J Respir Cell Mol Biol* 2006; 34:766-774.
20. Meisel C, Schefold J C, Pschowski R, Baumann H, Hetzger K, Gregor J, Weber-Carstens S, Hasper D, Keh D, Zuckermann H, et al. Granulocyte-macrophage colony-stimulating factor to reverse sepsis-associated immunosuppression: a double-blind, randomized, placebo-controlled multicenter trial. *Am J Respir Crit Care Med* 2009; 180:640-648.
21. Paine R, III, Preston A M, Wilcoxen S, Jin H, Siu B B, Morris S B, Reed J A, Ross G, Whitsett J A, and Beck J M. Granulocyte-macrophage colony-stimulating factor in the innate immune response to *Pneumocystis carinii* pneumonia in mice. *J Immunol* 2000; 164:2602-2609.
22. Orson F M, Kinsey B M, Densmore C L, Nguyen T, Wu Y, Mbawuike I N, and Wyde P R. Protection against influenza infection by cytokine-enhanced aerosol genetic immunization. *J Gene Med* 2006; 8:488-497.
23. Huang H, Li H, Zhou P, and Ju D. Protective effects of recombinant human granulocyte macrophage colony stimulating factor on H1N1 influenza virus-induced pneumonia in mice. *Cytokine* 2010; 51:151-157.
24. Huffman Reed J A, Rice W R, Zsengeller Z K, Wert S E, Dranoff G, and Whitsett J A. GM-CSF enhances lung growth and causes alveolar type II epithelial cell hyperplasia in transgenic mice. *Am J Physiol* 1997; 273:L715-L725.
25. Ye J, Sorrell E M, Cai Y, Shao H, Xu K, Pena L, Hickman D, Song H, Angel M, Medina R A, et al. Variations in the Hemagglutinin of the 2009 H1N1 Pandemic Virus: Potential for Strains with Altered Virulence Phenotype? *PLoS Pathog* 2010; 6:e1001145.
26. LeVine A M, Whitsett J A, Hartshorn K L, Crouch E C, and Korfhagen T R. Surfactant protein D enhances clearance of influenza A virus from the lung in vivo. *J Immunol* 2001; 167:5868-5873.
27. Orson F M, Kinsey B M, Hua P J, Bhogal B S, Densmore C L, and Barry M A. Genetic immunization with lung-targeting macroaggregated polyethyleneimine-albumin conjugates elicits combined systemic and mucosal immune responses. *J Immunol* 2000; 164:6313-6321.
28. Durbin J E, Fernandez-Sesma A, Lee C K, Rao T D, Frey A B, Moran T M, Vukmanovic S, Garcia-Sastre A, and Levy D E. Type I IFN modulates innate and specific antiviral immunity. *J Immunol* 2000; 164:4220-4228.
29. Wyde P R, Wilson M R, and Cate T R. Interferon production by leukocytes infiltrating the lungs of mice during primary influenza virus infection. *Infect Immun* 1982; 38:1249-1255.
30. Holt P G and Strickland D H. The CD200-CD200R axis in local control of lung inflammation. *Nat Immunol* 2008; 9:1011-1013.
31. Snelgrove R J, Goulding J, Didierlaurent A M, Lyonga D, Vekaria S, Edwards L, Gwyer E, Sedgwick J D, Barclay A N, and Hussell T. A critical function for CD200 in lung immune homeostasis and the severity of influenza infection. *Nat Immunol* 2008; 9:1074-1083.
32. Berg J T, Lee S T, Thepen T, Lee C Y, and Tsan M F. Depletion of alveolar macrophages by liposome-encapsulated dichloromethylene diphosphonate. *J Appl Physiol* 1993; 74:2812-2819.
33. Tyner J W, Uchida O, Kajiwara N, Kim E Y, Patel A C, O'Sullivan M P, Walter M J, Schwendener R A, Cook D N, Danoff T M, et al. CCL5-CCR5 interaction provides anti-apoptotic signals for macrophage survival during viral infection. *Nat Med* 2005; 11:1180-1187.
34. Dessing M C, van der Sluijs K F, Florquin S, and van der P T. Monocyte chemoattractant protein 1 contributes to an adequate immune response in influenza pneumonia. *Clin Immunol* 2007; 125:328-336.
35. Narasaraju T, Ng H H, Phoon M C, and Chow V T. MCP-1 antibody treatment enhances damage and impedes repair of the alveolar epithelium in influenza pneumonitis. *Am J Respir Cell Mol Biol* 2010; 42:732-743.

36. Hui K P, Lee S M, Cheung C Y, Ng I H, Poon L L, Guan Y, Ip N Y, Lau A S, and Peiris J S. Induction of proinflammatory cytokines in primary human macrophages by influenza A virus (H5N1) is selectively regulated by IFN regulatory factor 3 and p38 MAPK. *J Immunol* 2009; 182:1088-1098.

37. Marsolais D, Hahm B, Walsh K B, Edelmann K H, McGavern D, Hatta Y, Kawaoka Y, Rosen H, and Oldstone M B. A critical role for the sphingosine analog AAL-R in dampening the cytokine response during influenza virus infection. *Proc Natl Acad Sci USA* 2009; 106:1560-1565.

38. Baskin C R, Bielefeldt-Ohmann H, Tumpey T M, Sabourin P J, Long J P, Garcia-Sastre A, Tolnay AE, Albrecht R, Pyles J A, Olson P H, et al. Early and sustained innate immune response defines pathology and death in nonhuman primates infected by highly pathogenic influenza virus. *Proc Natl Acad Sci USA* 2009; 106:3455-3460.

39. Hussell T, Pennycook A, and Openshaw P J Inhibition of tumor necrosis factor reduces the severity of virus-specific lung immunopathology. *Eur J Immunol* 2001; 31:2566-2573.

40. Seo S H and Webster R G. Tumor necrosis factor alpha exerts powerful anti-influenza virus effects in lung epithelial cells. *J Virol* 2002; 76:1071-1076.

41. Tuvim M J, Evans S E, Clement C G, Dickey B F, and Gilbert B E. Augmented lung inflammation protects against influenza A pneumonia. *PLoS ONE* 2009; 4:e4176.

42. Sun J. Effector T cells control lung inflammation during acute influenza virus infection by producing IL-10.2009.

43. Tate M D, Pickett D L, van R N, Brooks A G, and Reading P C. Critical role of airway macrophages in modulating disease severity during influenza virus infection of mice. *J Virol* 2010; 84:7569-7580.

44. Benne C A, Benaissa-Trouw B, van Strijp J A, Kraaijeveld C A, and van Iwaarden J F. Surfactant protein A, but not surfactant protein D, is an opsonin for influenza A virus phagocytosis by rat alveolar macrophages. *Eur J Immunol* 1997; 27:886-890.

45. Mok C K, Lee D C, Cheung C Y, Peiris M, and Lau A S. Differential onset of apoptosis in influenza A virus. *J Gen Virol* 2007; 88:1275-1280.

46. Berclaz P Y, Zsengeller Z, Shibata Y, Otake K, Strasbaugh S, Whitsett J A, and Trapnell B C. Endocytic internalization of adenovirus, nonspecific phagocytosis, and cytoskeletal organization are coordinately regulated in alveolar macrophages by GM-CSF and P U.1. *J Immunol* 2002; 169: 6332-6342.

47. LeVine A M, Reed J A, Kurak K E, Cianciolo E, and Whitsett J A. GM-CSF-deficient mice are susceptible to pulmonary group B streptococcal infection. *J Clin Invest* 1999; 103:563-569.

48. Shibata Y, Berclaz P Y, Chroneos Z C, Yoshida M, Whitsett J A, and Trapnell B C. GM-CSF regulates alveolar macrophage differentiation and innate immunity in the lung through P U.1. *Immunity* 2001; 15:557-567.

49. Paine R, III, Wilcoxen S E, Morris S B, Sartori C, Baleeiro C E, Matthay M A, and Christensen P J. Transgenic overexpression of granulocyte macrophage-colony stimulating factor in the lung prevents hyperoxic lung injury. *Am J Pathol* 2003; 163:2397-2406.

50. Xing Z, Cardona C J, Adams S, Yang Z, Li J, Perez D, and Woolcock P R. Differential regulation of antiviral and proinflammatory cytokines and suppression of Fas-mediated apoptosis by NS1 of H9N2 avian influenza virus in chicken macrophages. *J Gen Virol* 2009; 90:1109-1118.

51. Chao J R, Wang J M, Lee S F, Peng H W, Lin Y H, Chou C H, Li J C, Huang H M, Chou C K, Kuo M L, et al. mcl-1 is an immediate-early gene activated by the granulocyte-macrophage colony-stimulating factor (GM-CSF) signaling pathway and is one component of the GM-CSF viability response. *Mol Cell Biol* 1998; 18:4883-4898.

52. Guthridge M A, Barry E F, Felquer F A, McClure B J, Stomski F C, Ramshaw H, and Lopez A F. The phosphoserine-585-dependent pathway of the GM-CSF/IL-3/IL-5 receptors mediates hematopoietic cell survival through activation of NF-κB and induction of bcl-2. *Blood* 2004; 103:820-827

---

What is claimed is:

1. A method of reducing influenza infection in a human subject, comprising administering to the lungs of a human subject in need thereof an effective amount of human granulocyte-macrophage colony stimulating factor (hGM-CSF) polypeptide having the amino acid sequence of SEQ ID NO:4, or a polypeptide having at least 95% sequence identity to SEQ ID NO:4.

2. The method according to claim 1, wherein said administration is by an intranasal or intrapulmonary route.

3. The method according to claim 1, wherein the hGM-CSF polypeptide is a recombinant hGM-CSF polypeptide.

4. The method according to claim 3, wherein the polypeptide is conjugated to polyethylene glycol (PEG).

5. The method according to claim 4 wherein the PEG is a polymer of about 12 monomeric units.

6. The method according to claim 3, wherein the polypeptide is conjugated to nanoparticles.

7. The method according to claim 6 wherein the nanoparticles have an average diameter of at least 10 nm.

8. The method according claim 1, wherein said hGM-CSF polypeptide is administered to a subject infected with influenza virus.

9. The method according to claim 1, wherein the polypeptide is conjugated to polyethylene glycol (PEG).

10. The method according to claim 9, wherein the PEG is a polymer of about 12 monomeric units.

11. The method according to claim 1, wherein the polypeptide is conjugated to nanoparticles.

12. The method according to claim 11, wherein the nanoparticles have an average diameter of at least 10 nm.

13. A method of stimulating innate immunity against influenza virus in the lungs of a human subject, comprising administering to the lungs of a human subject in need thereof an effective amount of hGM-CSF polypeptide having the amino acid sequence of SEQ ID NO:4, or a polypeptide having at least 95% sequence identity to SEQ ID NO:4 which stimulated innate immunity reduces development of influenza infection in said subject.

14. A method of stimulating influenza-resisting activity of alveolar macrophages in the lungs of a human subject, comprising administering to the lungs of a human subject in need thereof an effective amount of hGM-CSF polypeptide having the amino acid sequence of SEQ ID NO:4, or a polypeptide having at least 95% sequence identity to SEQ ID NO:4 wherein said stimulated alveolar macrophages reduce development of influenza infection in the subject.

* * * * *

SEQUENCE LISTING

```
<160> NUMBER OF SEQ ID NOS: 6

<210> SEQ ID NO 1
<211> LENGTH: 423
<212> TYPE: DNA
<213> ORGANISM: Mus musculus
<220> FEATURE:
<223> OTHER INFORMATION: murine granulocyte-macrophage colony
      stimulating factor e(GM-CSFe)

<400> SEQUENCE: 1
atgtggctgc agaatttact tttcctgggc attgtggtct acagcctctc agcacccacc        60
cgctcaccca tcactgtcac ccggccttgg aagcatgtag aggccatcaa agaagccctg       120
aacctcctgg atgacatgcc tgtcacgttg aatgaagagg tagaagtcgt ctctaacgag       180
ttctccttca agaagctaac atgtgtgcag acccgcctga agatattcga gcagggtcta       240 cgggggcaatt tcaccaaact caagggcgcc ttgaacatga cagccagcta ctaccagaca       300
tactgccccc caactccgga aacggactgt gaaacacaag ttaccaccta tgcggatttc       360
atagacagcc ttaaaacctt tctgactgat atcccctttg aatgcaaaaa accaggccaa       420
aaa                                                                      423
```

<210> SEQ ID NO 2
<211> LENGTH: 141
<212> TYPE: PRT
<213> ORGANISM: Mus musculus
<220> FEATURE:
<223> OTHER INFORMATION: murine granulocyte-macrophage colony
      stimulating factor (GM-CSF)

<400> SEQUENCE: 2

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140

<210> SEQ ID NO 3
<211> LENGTH: 432
<212> TYPE: DNA
<213> ORGANISM: Homo sapiens
<220> FEATURE:
<223> OTHER INFORMATION: human GM-CSF

<400> SEQUENCE: 3
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga atgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagat tatcaccttt     360
gaaagtttca agagaaacct gaaggacttt ctgcttgtca tccccttga ctgctgggag     420 ccagtccagg ag                                                         432

<210> SEQ ID NO 4
<211> LENGTH: 144
<212> TYPE: PRT
<213> ORGANISM: Homo sapiens
<220> FEATURE:
<223> OTHER INFORMATION: human GM-CSF

<400> SEQUENCE: 4

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

```
Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
               100                 105                 110

Cys Ala Thr Gln Ile Ile Thr Phe Glu Ser Phe Lys Glu Asn Leu Lys
               115                 120                 125

Asp Phe Leu Leu Val Ile Pro Phe Asp Cys Trp Glu Pro Val Gln Glu
           130                 135                 140

<210> SEQ ID NO 5
<211> LENGTH: 400
<212> TYPE: PRT
<213> ORGANISM: Homo sapiens
<220> FEATURE:
<223> OTHER INFORMATION: transcription variant of human GM-CSF receptor

<400> SEQUENCE: 5

Met Leu Leu Leu Val Thr Ser Leu Leu Leu Cys Glu Leu Pro His Pro
 1               5                  10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
            35                  40                  45

Trp Asp Cys Gln Glu Asn Thr Thr Phe Ser Lys Cys Phe Leu Thr Asp
 50                  55                  60

Lys Lys Asn Arg Val Val Glu Pro Arg Leu Ser Asn Asn Glu Cys Ser
 65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
               100                 105                 110

Asn Ser Gly Arg Glu Gly Thr Ala Ala Gln Asn Phe Ser Cys Phe Ile
           115                 120                 125

Tyr Asn Ala Asp Leu Met Asn Cys Thr Trp Ala Arg Gly Pro Thr Ala
           130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
               165                 170                 175

Gly Cys His Leu Asp Asn Leu Ser Gly Leu Thr Ser Arg Asn Tyr Phe
           180                 185                 190

Leu Val Asn Gly Thr Ser Arg Glu Ile Gly Ile Gln Phe Phe Asp Ser
           195                 200                 205

Leu Leu Asp Thr Lys Lys Ile Glu Arg Phe Asn Pro Pro Ser Asn Val
       210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
               245                 250                 255
```

```
Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
            275                 280                 285

Arg Ala Lys His Ser Val Lys Ile Arg Ala Ala Asp Val Arg Ile Leu
            290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
            325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
            355                 360                 365

Asn His Glu Val Glu Asp Glu Ile Ile Trp Glu Glu Phe Thr Pro Glu
            370                 375                 380

Glu Gly Lys Gly Tyr Arg Glu Glu Val Leu Thr Val Lys Glu Ile Thr
385                 390                 395                 400

<210> SEQ ID NO 6
<211> LENGTH: 375
<212> TYPE: PRT
<213> ORGANISM: Homo sapiens
<220> FEATURE:
<223> OTHER INFORMATION: transcription variant of human GM-CSF receptor

<400> SEQUENCE: 6

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
            35                  40                  45

Trp Asp Cys Gln Glu Asn Thr Thr Phe Ser Lys Cys Phe Leu Thr Asp
        50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
            115                 120                 125

Tyr Asn Ala Asp Leu Met Asn Cys Thr Trp Ala Arg Gly Pro Thr Ala
        130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
            195                 200                 205

Leu Leu Asp Thr Lys Lys Ile Glu Arg Phe Asn Pro Pro Ser Asn Val
        210                 215                 220
```

-continued

```
Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
                260                 265                 270

Val Ser Gly Asp Leu Glu Asn Arg Tyr Asn Phe Pro Ser Ser Glu Pro
            275                 280                 285

Arg Ala Lys His Ser Val Lys Ile Arg Ala Ala Asp Val Arg Ile Leu
        290                 295                 300

Asn Trp Ser Ser Trp Ser Glu Ala Ile Glu Phe Asp His Leu Gly Gly
305                 310                 315                 320

Ile His Pro Arg Gly Arg Glu Arg Leu Pro Arg Arg Gly Leu Asp Arg
                325                 330                 335

Glu Gly Asn Tyr Leu Arg Pro Arg Gly Cys Arg Asn Gly Met Asp Ile
                340                 345                 350

Ser Ala Ser Ala Thr Arg Gly Asn Phe Leu Asp Asp Ala Val Asn Leu
            355                 360                 365

Tyr Ile Phe Tyr Val Phe Ile
            370             375
```